US010800732B2

United States Patent
Shiau et al.

(10) Patent No.: US 10,800,732 B2
(45) Date of Patent: Oct. 13, 2020

(54) SUBSTITUTED MALONAMIDES AND THEIR USE AS ANTIBACTERIAL DRUGS

(71) Applicant: National Taiwan University, Taipei (TW)

(72) Inventors: Chung-Wai Shiau, Taipei (TW); Hao-Chieh Chiu, Taipei (TW)

(73) Assignees: NATIONAL TAIWAN UNIVERSITY, Taipei (TW); NATIONAL YANG-MING UNIVERSITY, Taipei (TW)

( * ) Notice: Subject to any disclaimer, the term of this patent is extended or adjusted under 35 U.S.C. 154(b) by 0 days.

(21) Appl. No.: 15/752,260

(22) PCT Filed: Aug. 12, 2016

(86) PCT No.: PCT/CN2016/094855
§ 371 (c)(1),
(2) Date: Feb. 13, 2018

(87) PCT Pub. No.: WO2017/028745
PCT Pub. Date: Feb. 23, 2017

(65) Prior Publication Data
US 2018/0237379 A1    Aug. 23, 2018

Related U.S. Application Data

(60) Provisional application No. 62/206,251, filed on Aug. 17, 2015.

(51) Int. Cl.
| | |
|---|---|
| *C07C 233/05* | (2006.01) |
| *C07C 233/06* | (2006.01) |
| *C07C 233/07* | (2006.01) |
| *C07C 231/02* | (2006.01) |
| *A61K 31/165* | (2006.01) |
| *A61K 31/16* | (2006.01) |
| *A61P 31/04* | (2006.01) |
| *C07C 233/59* | (2006.01) |
| *C07C 233/09* | (2006.01) |
| *C07C 233/15* | (2006.01) |
| *C07C 233/25* | (2006.01) |
| *C07C 381/00* | (2006.01) |
| *C07C 233/58* | (2006.01) |

(52) U.S. Cl.
CPC .......... *C07C 233/59* (2013.01); *A61K 31/165* (2013.01); *A61P 31/04* (2018.01); *C07C 231/02* (2013.01); *C07C 233/05* (2013.01); *C07C 233/06* (2013.01); *C07C 233/07* (2013.01); *C07C 233/09* (2013.01); *C07C 233/15* (2013.01); *C07C 233/25* (2013.01); *C07C 233/58* (2013.01); *C07C 381/00* (2013.01); *C07C 2601/02* (2017.05); *C07C 2601/14* (2017.05)

(58) Field of Classification Search
CPC ... C07C 233/07; C07C 231/02; A61K 31/165; A61K 31/04; A61P 31/04
USPC .......................................... 564/160; 514/616
See application file for complete search history.

(56) References Cited

U.S. PATENT DOCUMENTS

| | | | | |
|---|---|---|---|---|
| 4,770,807 A | * | 9/1988 | Musikas ............. | C01F 17/0006 252/184 |
| 5,223,232 A | * | 6/1993 | Cuillerdier .......... | C01F 17/0006 210/634 |

FOREIGN PATENT DOCUMENTS

| | | |
|---|---|---|
| GB | 774802 A | 5/1957 |
| WO | 2017/207556 A4 | 12/2017 |

OTHER PUBLICATIONS

Moldaver et al. Khimiya Geterotsiklicheskikh Soedinenii, 7(5), 651-652, 1971; CA 76: 59518,197S2. CAPLUS Abstract provided.*
Kandiah et al. Journal of the Chemical Society, 922-52,1931.: CA 25:30065,1931.*
J. C. Wen et al., Synthesis and anti-tumor activity of S-hexyl(heptyl) substituted ethanethioate derivatives, Acta Pharmaceutica 2014, 49(3): 352-358 (including English translation).
R. Oeis et al., Reinvestigateion of the synthesis of 3-Dimethylallyl-4-hydroxy-2-quinolones. A Novel Route to Tetracyclic Heteroaromatic Compounds, J.C.S. Perkirc I, 1997, p. 2546-2551.
T. Kappe et al., Synthesis of benzo-halogenated 4-hydroxy-2(1H)-quinolones, Journal of Heterocyclic Chemistry, 1988, May/Jun. 25, p. 857-862.
Andr'e Daubinet and Perry T. Kaye, Designer ligands. VIII. thermal and microwave-assisted synthesis of silver(I)-selective ligands,Synthetic Communications, vol. 32, No. 20, Dec. 31, 2002, p. 3207-3217.
S. S. Block, Antibacterial and antifungal activity of Kepone derivatives, Developments in Industrial Microbiology, Elsevier Science BV, Amsterdam, NL, vol. 9, 1968, pp. 430-436, xp009510118, ISSN:0070-4563.
H C Chang et al., In vitro and in vivo activity of a novel sorafenib derivative SC5005 against MRSA, J Antimicrob Chemother 2016; 71: 449-459.

* cited by examiner

*Primary Examiner* — Venkataraman Balasubramanian
(74) *Attorney, Agent, or Firm* — Hannah Tien

(57) ABSTRACT

Disclosed are a series of malonamide derivatives having a chemical structure(I), their synthesis, and evaluation of their bioactivities against bacterial cell, bacterial-infected *C. elegans* and mice.

12 Claims, 10 Drawing Sheets
(1 of 10 Drawing Sheet(s) Filed in Color)

(A)

(B)

SUBSTITUTED MALONAMIDES AND THEIR USE AS ANTIBACTERIAL DRUGS

CROSS-REFERENCES TO RELATED APPLICATIONS

This patent application is a U.S. National Stage Application of PCT/CN2016/094855 filed on Aug. 12, 2016 and claims the benefit of priority from U.S. Provisional Application Ser. No. 62/206,251 filed on Aug. 17, 2015, the contents of each of which is incorporated herein by reference in their entirety.

BACKGROUND OF THE INVENTION

Technical Field

The disclosure relates to malonamide derivatives and their use as antibacterial drugs.

Description of Related Art

*Staphylococcus aureus*, a Gram-positive bacterium, is frequently found on the skin, skin glands and mucous membranes of humans and can cause a variety of illnesses, from minor skin infection, cellulitis and abscesses to life-threatening bacteraemia, pneumonia, endocarditis and osteomyelitis. Due to its strong pathogenicity, *S. aureus* has always been the leading causative agent of hospital- and community-acquired infections in developed countries. In the USA, it is estimated that the number of deaths caused by *S. aureus* infection is greater than the sum of those from HIV, viral hepatitis, TB and influenza. Initially, infection with *S. aureus* could be effectively treated with b-lactam antibiotics. However, the emergence of b-lactam-resistant *S. aureus* strains, including MRSA, was reported in the 1950s and soon became endemic in many hospitals worldwide. In addition to b-lactam antibiotics, *S. aureus* has developed resistance to several other classes of antibiotics, including aminoglycosides, macrolides, lincosamides, chloramphenicol, sulphonamides, streptomycin and tetracycline. Moreover, strains of *S. aureus* resistant to second-line antibiotics, including linezolid, daptomycin and vancomycin, have also been reported in the past few years. The capability of *S. aureus* to resist multiple antibiotics has rendered its treatment difficult, leading to longer hospitalizations and higher mortality in patients. Thus, development of new antibacterial agents against *S. aureus*, especially strains resistant to multiple antibiotics, has become an urgent public health need.

The discovery of penicillin and streptomycin opened the golden era of antibiotics, which were mainly identified from substances produced by microorganisms living in soil. However, due to the widespread prevalence of antibiotic-resistant bacteria and the drop in new antibiotics identified from natural products, other sources of new antibacterial agents are being investigated. One such alternative source is through exploitation of the antibacterial activities of a group of drugs called 'non-antibiotics'. Non-antibiotics are drugs, usually synthetic, that were originally invented and used for the therapy of non-infectious diseases, but were subsequently discovered to possess certain antimicrobial activities. For example, statins, a class of cholesterol synthesis inhibitors, were shown to suppress the virulence of *S. aureus* by inducing the antimicrobial activity of phagocytes. Another example is the phenothiazines, a group of antipsychotic agents, which have been shown to exhibit activity against a variety of bacteria. Moreover, a recent clinical study demonstrated that thioridazine, one of the phenothiazines, can act synergistically with antibiotics to eradicate TB from patients infected with XDR *Mycobacterium tuberculosis*. Thus, non-antibiotic drugs represent a promising source for the discovery and development of novel antibacterial agents.

New malonamide derivatives were discovered to possess suppressive effects on the growth of *S. aureus*, and *S. epidermidis*. Our efforts have led to the identification of a novel agent that exhibit high anti-MRSA potency without acute cytotoxicity against human cells.

BRIEF SUMMARY OF THE INVENTION

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present invention is directed to a substituted malonamide having a chemical structure (I):

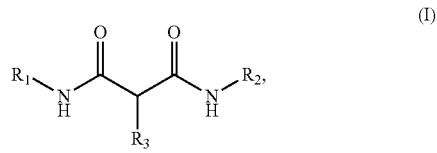

wherein $R_1$ is

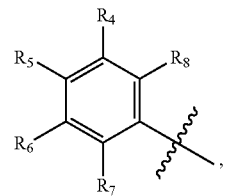

$C_{2-6}$ alkyl, $C_{2-6}$ alkenyl, or $C_{3-7}$ cycloalkyl;
$R_2$ is

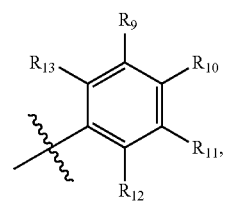

$C_{2-6}$ alkyl, $C_{2-6}$ alkenyl, or $C_{3-7}$ cycloalkyl;
$R_3$ is selected from $C_3$ cycloalkyl, $C_{2-6}$ alkenyl, or $C_{2-5}$ halogenoalkyl;
$R_4$, $R_5$, $R_6$, $R_7$, $R_8$, $R_9$, $R_{10}$, $R_{11}$, $R_{12}$, and $R_{13}$ are independently selected from hydrogen, C1-5 alkyl, C2-6 alkenyl, halogen, trihalogenomethyl, nitro, hydroxyl, trihalogenomethoxy, or pentafluorosulfanyl.

In yet another aspect, the present invention is directed to pharmaceutical composition comprising: an effective amount of a compound having a chemical structure (I):

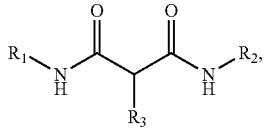
(I)

wherein $R_1$ is

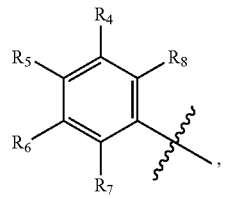

$C_{2-6}$ alkyl, $C_{2-6}$ alkenyl, or $C_{3-7}$ cycloalkyl;

$R_2$ is

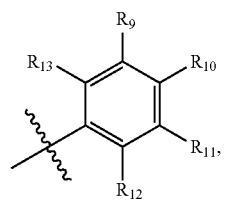

$C_{2-6}$ alkyl, $C_{2-6}$ alkenyl, or $C_{3-7}$ cycloalkyl;

$R_3$ is selected from $C_3$ cycloalkyl, $C_{2-6}$ alkenyl, or $C_{2-5}$ halogenoalkyl;

$R_4$, $R_5$, $R_6$, $R_7$, $R_8$, $R_9$, $R_{10}$, $R_{11}$, $R_{12}$, and $R_{13}$ are independently selected from hydrogen, $C_{1-5}$ alkyl, $C_{2-6}$ alkenyl, halogen, trihalogenomethyl, nitro, hydroxyl, trihalogenomethoxy, or pentafluorosulfanyl.

In yet another aspect, the present invention directs to a method of inhibiting a bacterial cell growth, comprising: contacting the bacterial cell with an effective amount of a compound having a chemical structure (I):

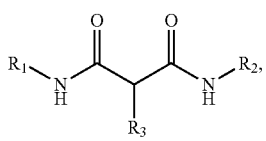
(I)

wherein $R_1$ is

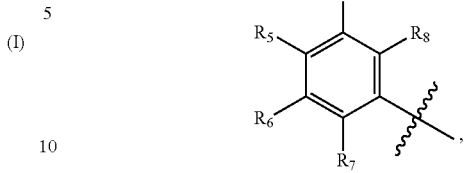

$C_{2-6}$ alkyl, $C_{2-6}$ alkenyl, or $C_{3-7}$ cycloalkyl;

$R_2$ is

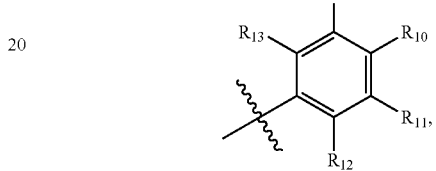

$C_{2-6}$ alkyl, $C_{2-6}$ alkenyl, or $C_{3-7}$ cycloalkyl;

$R_3$ is selected from $C_3$ cycloalkyl, $C_{2-6}$ alkenyl, or $C_{2-5}$ halogenoalkyl;

$R_4$, $R_5$, $R_6$, $R_7$, $R_8$, $R_9$, $R_{10}$, $R_{11}$, $R_{12}$, and $R_{13}$ are independently selected from hydrogen, $C_{1-5}$ alkyl, $C_{2-6}$ alkenyl, halogen, trihalogenomethyl, nitro, hydroxyl, trihalogenomethoxy, or pentafluorosulfanyl, or an effective amount of a compound having a chemical structure (IV):

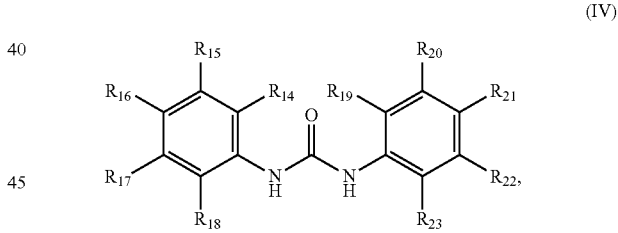
(IV)

wherein $R_{14}$, $R_{15}$, $R_{16}$, $R_{17}$, $R_{18}$, $R_{19}$, $R_{20}$, $R_{21}$, $R_{22}$, and $R_{23}$ are independently selected from hydrogen, halogen, or trihalogenomethyl.

In yet another aspect, the present invention directs to a method of synthesizing the substituted malonamide of the present invention, comprising: (a) reacting a compound having chemical structure (II) with a first substituted amine $R_1$—$NH_2$ to obtain a compound having chemical structure (III),

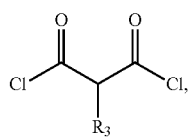
(II)

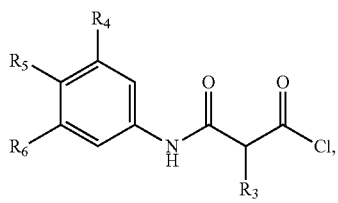

(b) the compound having chemical structure (III) further reacts with a second substituted amine $R_2$—$NH_2$ to obtain the substituted malonamide of the present invention, wherein $R_1$ is

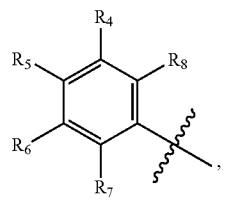

$C_{2-6}$ alkyl, $C_{2-6}$ alkenyl, or $C_{3-7}$ cycloalkyl;
$R_2$ is

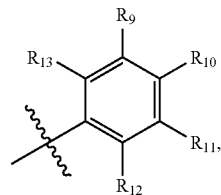

$C_{2-6}$ alkyl, $C_{2-6}$ alkenyl, or $C_{3-7}$ cycloalkyl;
$R_3$ is selected from $C_3$ cycloalkyl, $C_{2-6}$ alkenyl, or $C_{2-5}$ halogenoalkyl;
$R_4$, $R_5$, $R_6$, $R_7$, $R_8$, $R_9$, $R_{10}$, $R_{11}$, $R_{12}$, and $R_{13}$ are independently selected from $C_{1-5}$ alkyl, $C_{2-6}$ alkenyl, halogen, trihalogenomethyl, nitro, hydroxyl, trihalogenomethoxy, or pentafluorosulfanyl.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
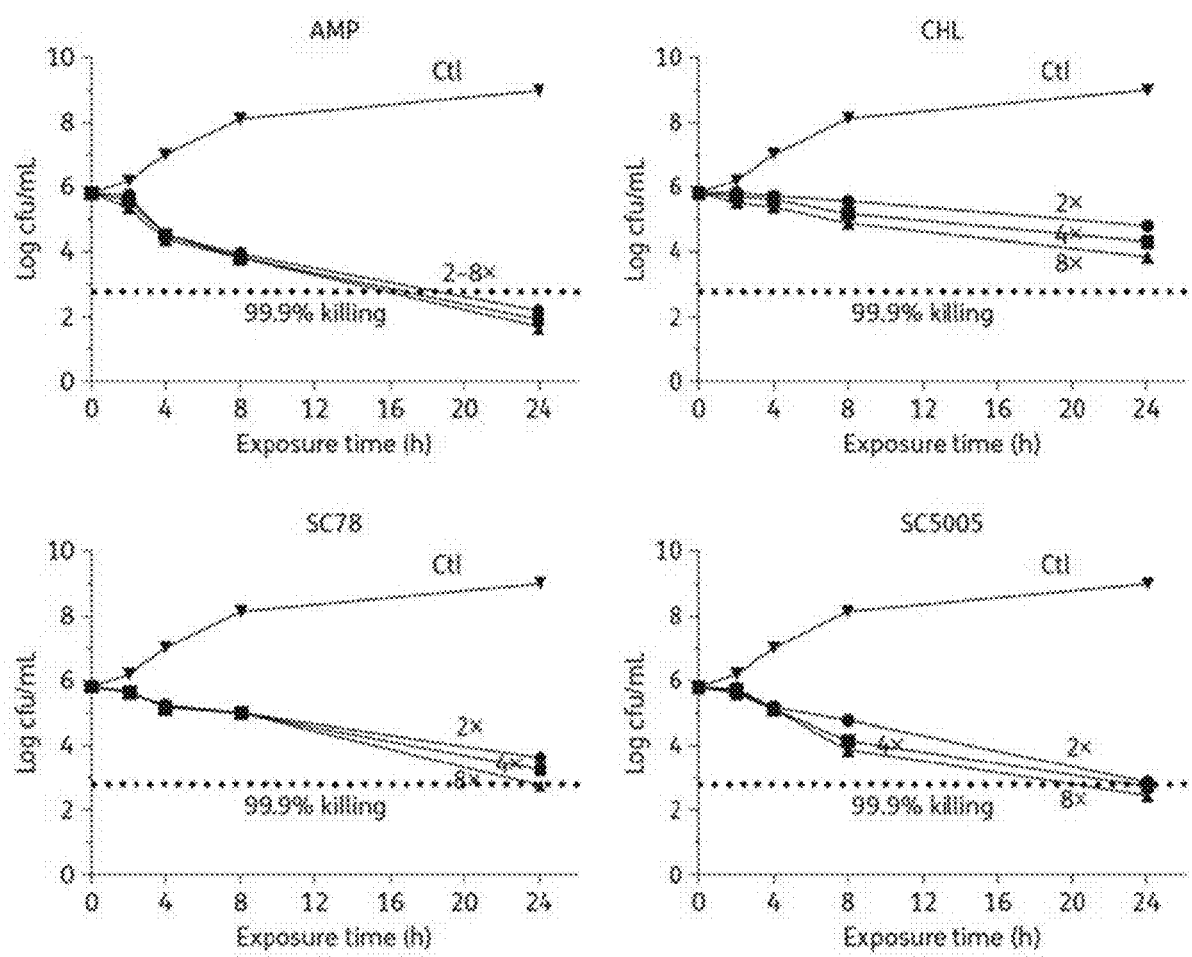
FIG. 1. Time-kill kinetics of SC78 and SC5005. The viability of *S. aureus* NCTC 8325 was assayed after exposure to 0×MIC (control) (filled inverted triangles), 2×MIC (filled circles), 4×MIC (filled squares) and 8×MIC (filled triangles) of ampicillin (upper left panel; MIC=0.25 mg/L), chloramphenicol (upper right panel; MIC=4 mg/L), SC78 (lower left panel; MIC=0.25 mg/L) and SC5005 (lower right panel; MIC=0.5 mg/L) for 2, 4, 8 and 24 h in CAMHB. Numbers of viable bacteria in the broth after each exposure period were enumerated by CFU assay and the results expressed as CFU/mL. Points indicate means and bars indicate SD (n=3); the bars cannot be seen because the SD of each point is very small. The broken horizontal line represents 99.9% cell killing. AMP, ampicillin; CHL, chloramphenicol; Ctl, control.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The following abbreviations are used: CDCl$_3$, deuterated chloroform; DMSO-d6, dimethyl sulfoxide-d6; i-PrOH, isopropyl alcohol; EtOAc, ethyl acetate; DMF, N,N-dimethylformamide; MeOH, methanol; THF, tetrahydrofuran; EtOH, ethanol; DMSO, dimethyl sulfoxide; DIPEA, diisopropylethylamine; DCM, dichloromethane.

The invention provides a substituted malonamide having a chemical structure (I):

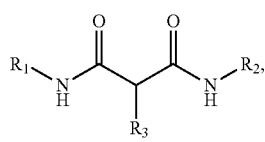

(I)

wherein $R_1$ is

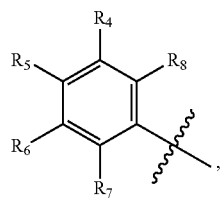

$C_{2-6}$ alkyl, $C_{2-6}$ alkenyl, or $C_{3-7}$ cycloalkyl;

$R_2$ is

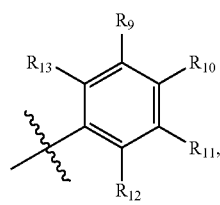

$C_{2-6}$ alkyl, $C_{2-6}$ alkenyl, or $C_{3-7}$ cycloalkyl;

$R_3$ is selected from $C_3$ cycloalkyl, $C_{2-6}$ alkenyl, or $C_{2-5}$ halogenoalkyl;

$R_4$, $R_5$, $R_6$, $R_7$, $R_8$, $R_9$, $R_{10}$, $R_{11}$, $R_{12}$, and $R_{13}$ are independently selected from hydrogen, $C_{1-5}$ alkyl, $C_{2-6}$ alkenyl, halogen, trihalogenomethyl, nitro, hydroxyl, trihalogenomethoxy, or pentafluorosulfanyl. In a preferred embodiment, $R_1$, and $R_2$ are independently selected from

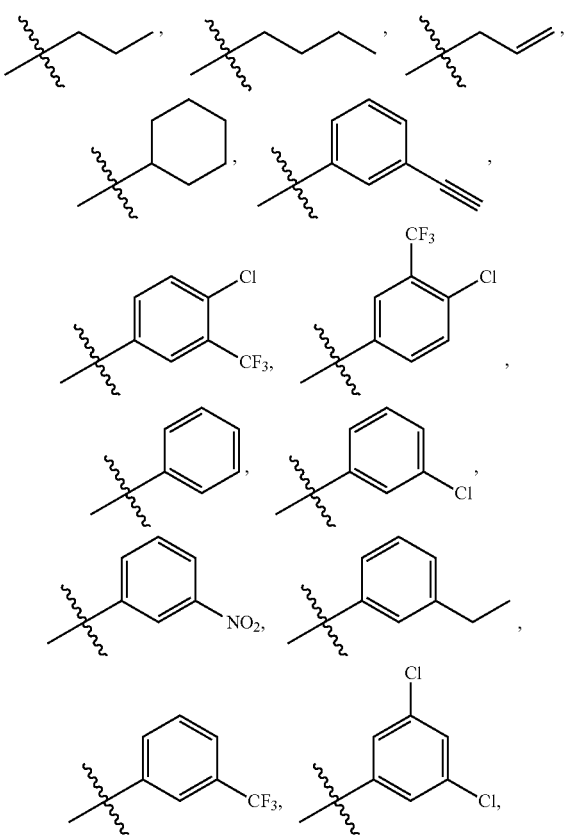

-continued

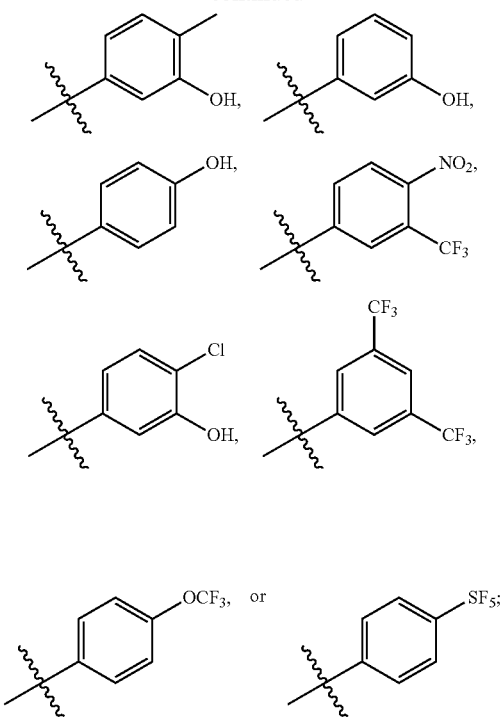

$R_3$ is selected from

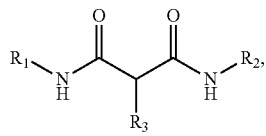

In a preferred embodiment, $R_1$, $R_2$, and $R_3$ are hydrophobic group.

The invention also provides a pharmaceutical composition comprising: an effective amount of a compound having a chemical structure (I):

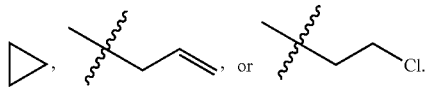

(I)

wherein $R_1$ is

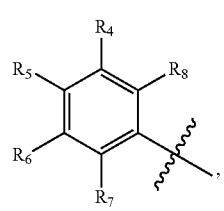

$C_{2-6}$ alkyl, $C_{2-6}$ alkenyl, or $C_{3-7}$ cycloalkyl;

$R_2$ is

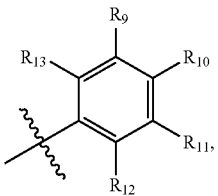

$C_{2-6}$ alkyl, $C_{2-6}$ alkenyl, or $C_{3-7}$ cycloalkyl;

$R_3$ is selected from $C_3$ cycloalkyl, $C_{2-6}$ alkenyl, or $C_{2-5}$ halogenoalkyl;

$R_4$, $R_5$, $R_6$, $R_7$, $R_8$, $R_9$, $R_{10}$, $R_{11}$, $R_{12}$, and $R_{13}$ are independently selected from hydrogen, $C_{1-5}$ alkyl, $C_{2-6}$ alkenyl, halogen, trihalogenomethyl, nitro, hydroxyl, trihalogenomethoxy, or pentafluorosulfanyl; and a pharmaceutically acceptable carrier. In a preferred embodiment, $R_1$, and $R_2$ are independently selected from

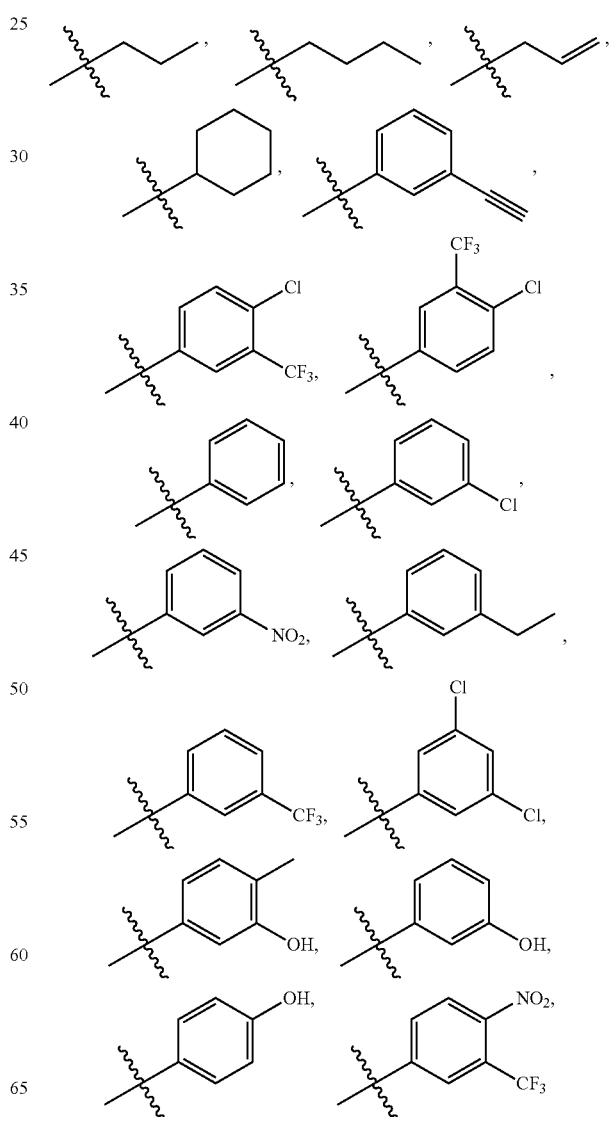

-continued

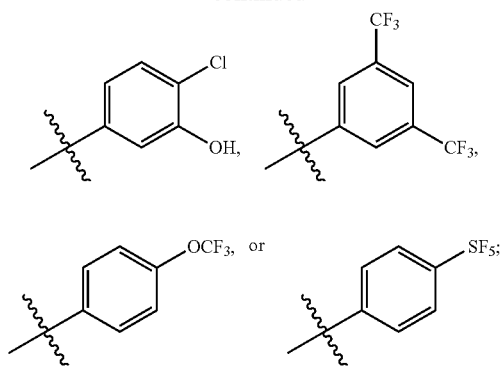

is selected from

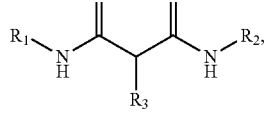

In another preferred embodiment, the compound having a chemical structure (I) is:

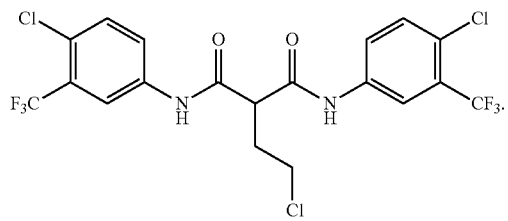
(V)

The invention also provides a method of inhibiting a bacterial cell growth, comprising: contacting the bacterial cell with an effective amount of a compound having a chemical structure (I):

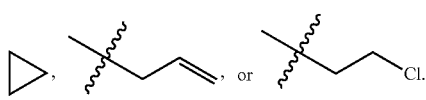
(I)

wherein $R_1$ is

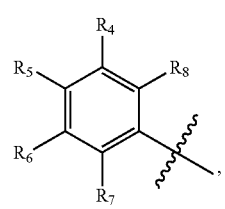

$C_{2-6}$ alkyl, $C_{2-6}$ alkenyl, or $C_{3-7}$ cycloalkyl;

$R_2$ is

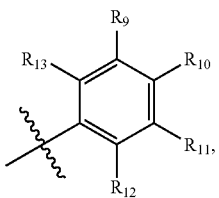

$C_{2-6}$ alkyl, $C_{2-6}$ alkenyl, or $C_{3-7}$ cycloalkyl;

$R_3$ is selected from $C_3$ cycloalkyl, $C_{2-6}$ alkenyl, or $C_{2-5}$ halogenoalkyl;

$R_4$, $R_5$, $R_6$, $R_7$, $R_8$, $R_9$, $R_{10}$, $R_{11}$, $R_{12}$, and $R_{13}$ are independently selected from hydrogen, $C_{1-5}$ alkyl, $C_{2-6}$ alkenyl, halogen, trihalogenomethyl, nitro, hydroxyl, trihalogenomethoxy, or pentafluorosulfanyl, or an effective amount of a compound having a chemical structure (IV):

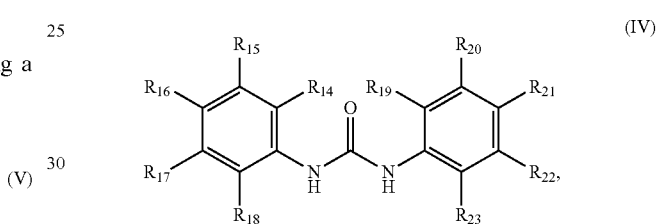
(IV)

wherein $R_{14}$, $R_{15}$, $R_{16}$, $R_{17}$, $R_{18}$, $R_{19}$, $R_{20}$, $R_{21}$, $R_{22}$, and $R_{23}$ are independently selected from hydrogen, halogen, or trihalogenomethyl.

In a preferred embodiment, $R_1$, and $R_2$ are independently selected from

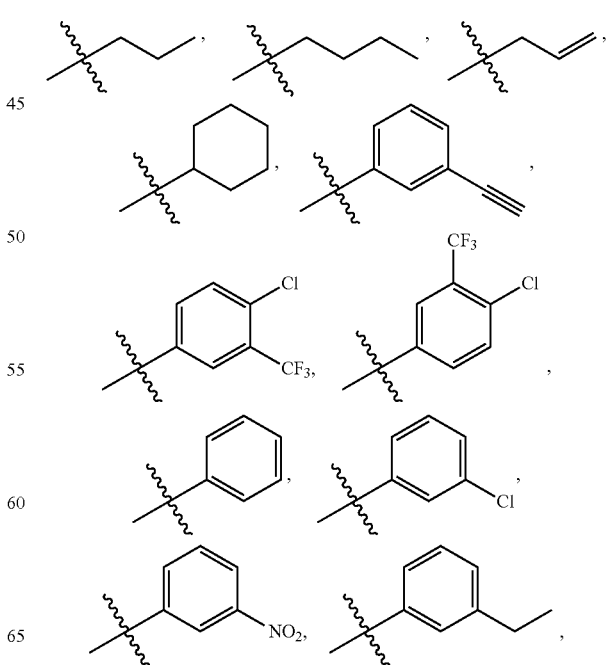

-continued

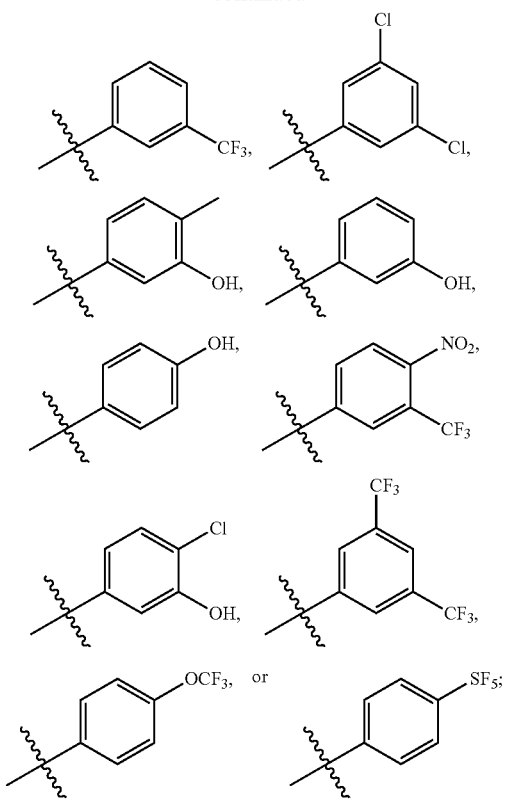

$R_3$ is selected from

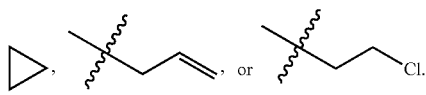

In another preferred embodiment, the compound having a chemical structure (I) is:

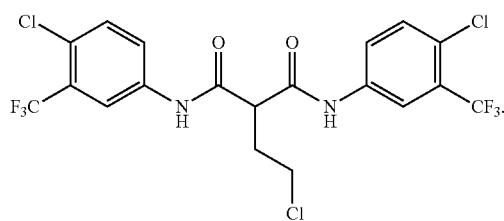
(V)

In another preferred embodiment, the compound having a chemical structure (IV) is:

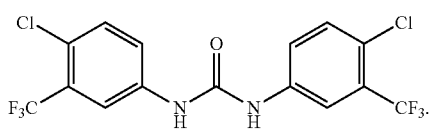
(VI)

In a preferred embodiment, the bacterial cell is cell of human pathogenic bacteria. The term "human pathogenic bacteria" means that the bacteria are pathogenic to humans. In another preferred embodiment, the human pathogenic bacteria are selected from the group consisting of *Staphylococcus aureus, S. haemolyticus, S. hominis, S. intermedius, S. saprophyticus, S. lugdunesis, Erysipelothrix rhusiopathiae, Enterococcus faecalis, Enterococcus faecium,* VR-*E. faecium, Bacillus cereus, Bacillus subtilis, Corynebacterium diphtheriae, Listeria monocytogenes, Streptococcus pyogenes, Clostridium difficile, Escherichia coli, Salmonella Typhimurium, Acinetobacter baumannii,* and *Mycobacterium tuberculosis.*

In another preferred embodiment, the bacteria above are a *Staphylococcus aureus* strains ATCC 12598, ATCC 29213, NCTC 8325, methicillin-resistant *Staphylococcus aureus* (MRSA) strains ATCC 33592, ATCC 49476, a clinically isolated MRSA strain carrying SCCmec $V_T$,[26] one hundred clinically isolated MRSA strains, a vanA-mediated vancomycin-resistant *Staphylococcus aureus* (VRSA) strain (SJC1200), and a clinical isolated vancomycin-intermediate *Staphylococcus aureus* (VISA) strain, *S. epidermidis* strains ATCC 35984 and ATCC 12228, *S. haemolyticus* strain ATCC 29970, *S. hominis* strain ATCC 27844, *S. intermedius* strain ATCC 29663, *S. saprophyticus* strain ATCC 15305, a clinically isolated *S. lugdunesis, Enterococcus faecalis* ATCC 19433, *Enterococcus faecium* ATCC 35667, *Enterococcus faecium* ATCC 19434, *Bacillus cereus* ATCC 11778, *Bacillus subtilis* BCRC 10255, *Corynebacterium diphtheria* ATCC 11913, *Listeria monocytogenes* ATCC 19113, *Erysipelothrix rhusiopathiae* ATCC 19414, *Streptococcus pyogenes* ATCC 19615, *Escherichia coli* ATCC 25922, *Salmonella Typhimurium* ATCC 14028, *Acinetobacter baumannii* BCRC 80276, a clinically isolated *S. lugdunesis,* and Vancomycin-Resistant *Enterococcus faecium* (VR-E).

The invention further provides a method of synthesizing the substituted malonamide of the present invention, comprising: reacting a compound having chemical structure (II) with a first substituted amine $R_1$—$NH_2$ to obtain a compound having chemical structure (III),

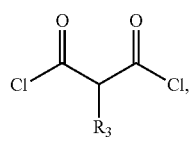
(II)

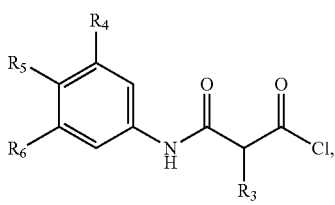
(III)

(b) the compound having chemical structure (III) further reacts with a second substituted amine $R_2$—$NH_2$ to obtain the substituted malonamide of the present invention, wherein $R_1$ is

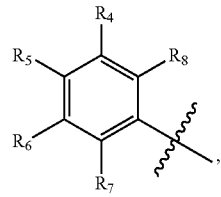

$C_{2-6}$ alkyl, $C_{2-6}$ alkenyl, or $C_{3-7}$ cycloalkyl;

$R_2$ is

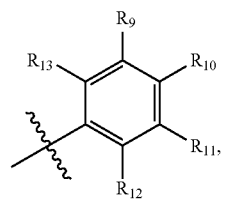

$C_{2-6}$ alkyl, $C_{2-6}$ alkenyl, or $C_{3-7}$ cycloalkyl;

$R_3$ is selected from $C_3$ cycloalkyl, $C_{2-6}$ alkenyl, benzyl, or $C_{2-5}$ halogenoalkyl;

$R_4$, $R_5$, $R_6$, $R_7$, $R_8$, $R_9$, $R_{10}$, $R_{11}$, $R_{12}$, and $R_{13}$ are independently selected from $C_{1-5}$ alkyl, $C_{2-6}$ alkenyl, halogen, trihalogenomethyl, nitro, hydroxyl, trihalogenomethoxy, or pentafluorosulfanyl.

In a preferred embodiment, $R_1$, and $R_2$ are independently selected from

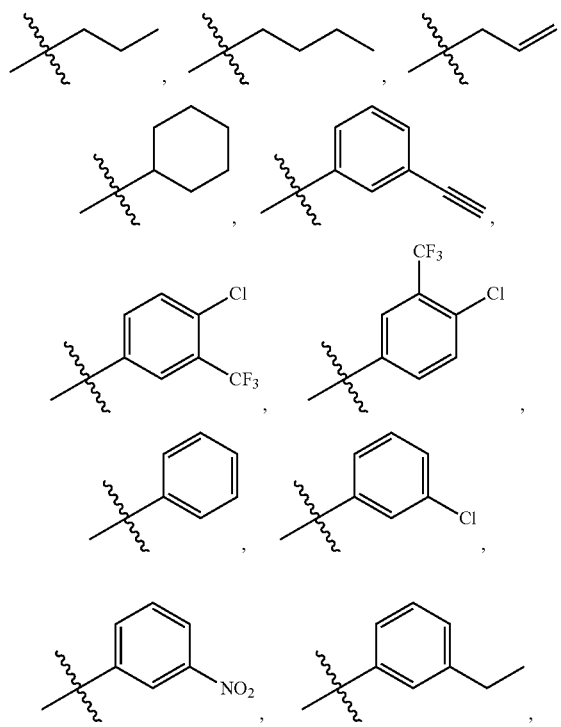

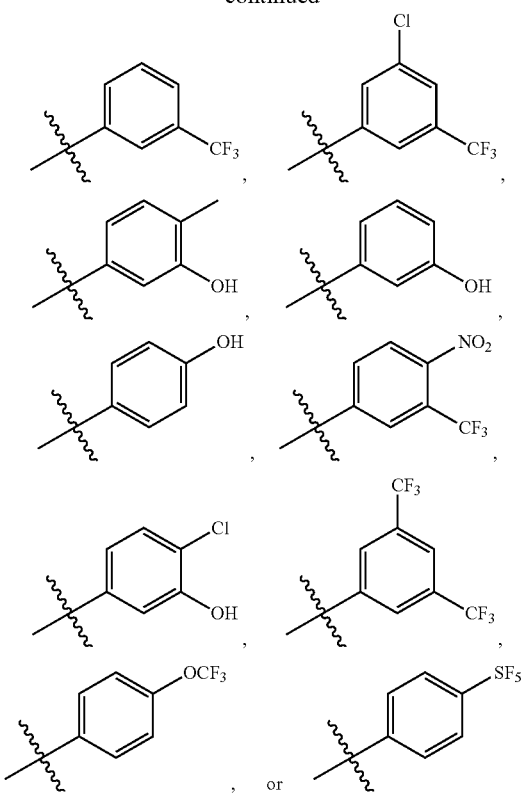

$R_3$ is selected from

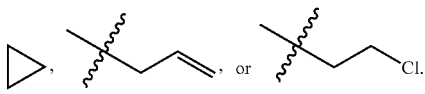

In yet another preferred embodiment, the present invention provides a method of synthesizing the substituted malonamide having the chemical structure (I). The method comprises the following steps. First, cyclopropane-1,1-dicarboxylic acid reacts with thionyl chloride to generate cyclopropane-1,1-dicarbonyl dichloride

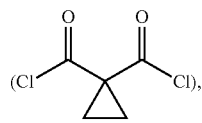

2-allylmalonyl dichloride

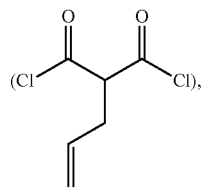

2-benzylmalonyl dichloride

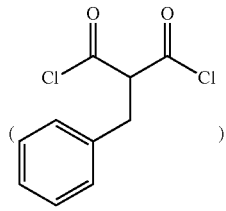 [SMILES: O=C(Cl)C(Cc1ccccc1)C(=O)Cl]

and 2-(2-chloroethyl)malonyl dichloride

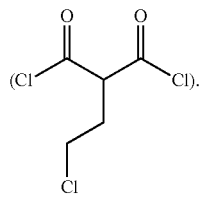

Second, cyclopropane-1,1-dicarbonyl dichloride or 2-(2-chloroethyl)malonyl dichloride reacts with 2 equivalence of substituted amines to form the chemical structure (I), wherein the two substituted phenyl amines having the two substituted phenyl group of,

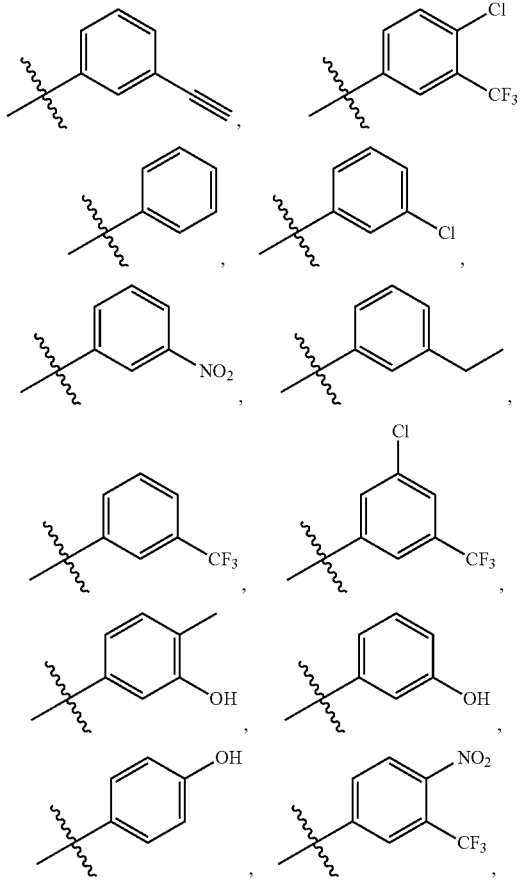

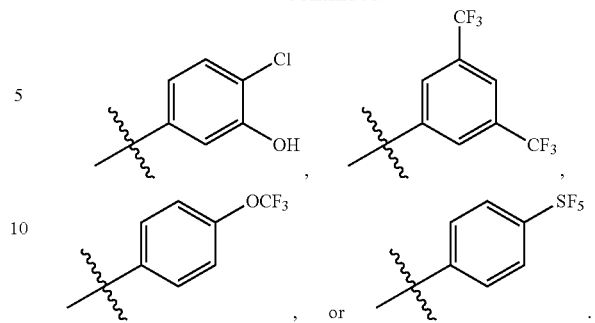

In yet another method, the compound of the cyclopropane-1,1-dicarbonyl dichloride or 2-(2-chloroethyl)malonyl dichloride reacts with the first substituted phenyl amine to form the compound of the chemical structure

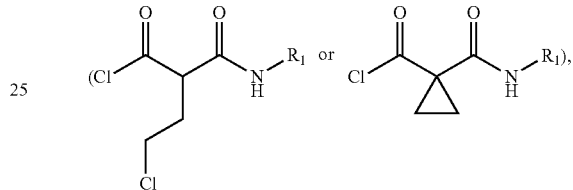

wherein the first substituted phenyl amine having a second substituted phenyl group of

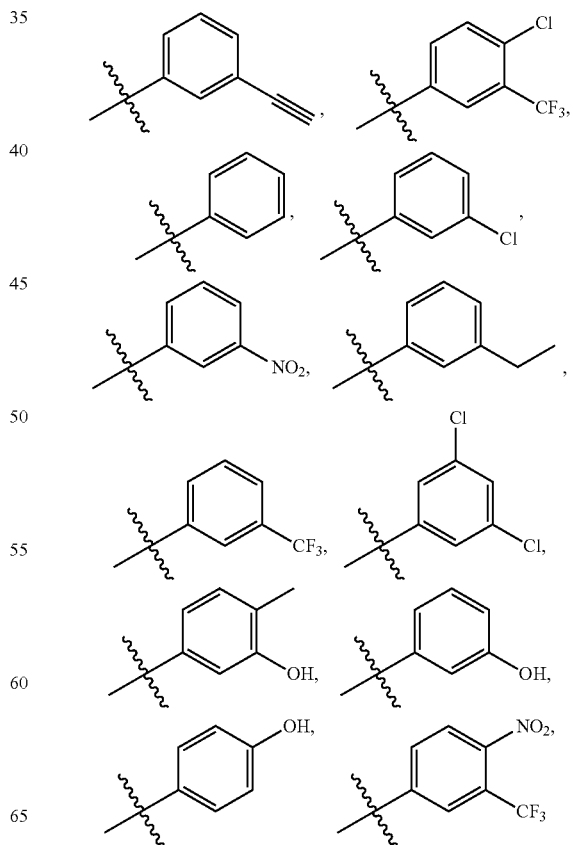

-continued
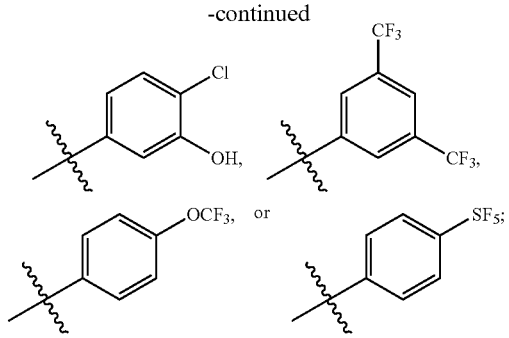
The result products further reacts with a second phenyl amine, wherein the second substituted phenyl amine having a second substituted phenyl group of,
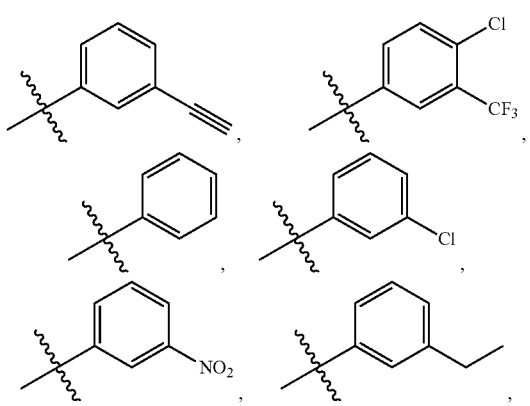
-continued
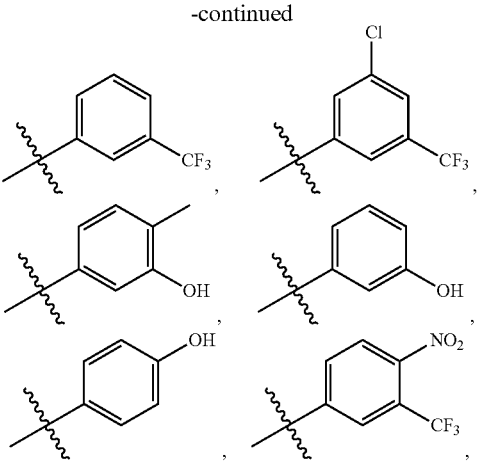
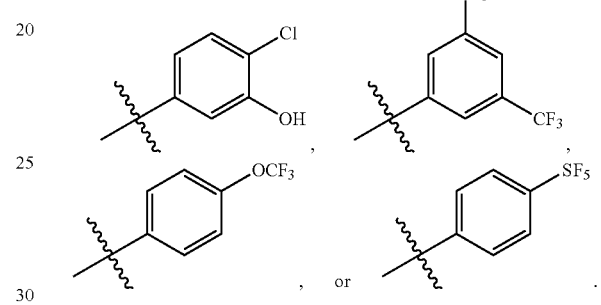
, or .
EXAMPLES
Synthesis of Malonamide Derivatives
Synthesis Scheme I
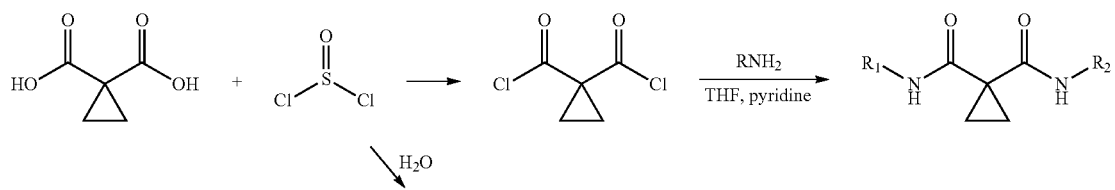
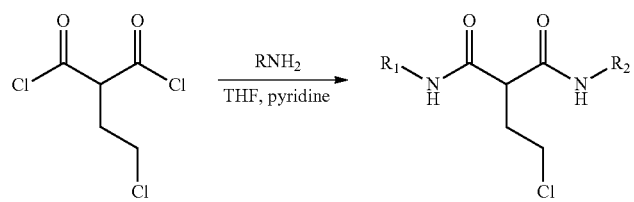
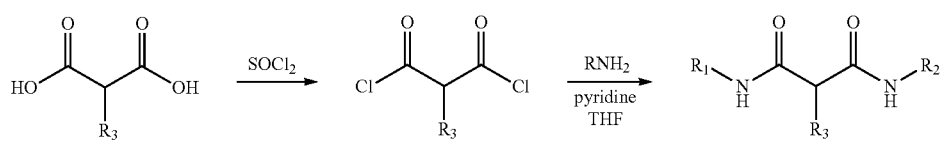

In the synthesis scheme I above, $R_1$ and $R_2$ can be the same or different substituted phenyl group. The $R_1$ and $R_2$ can be

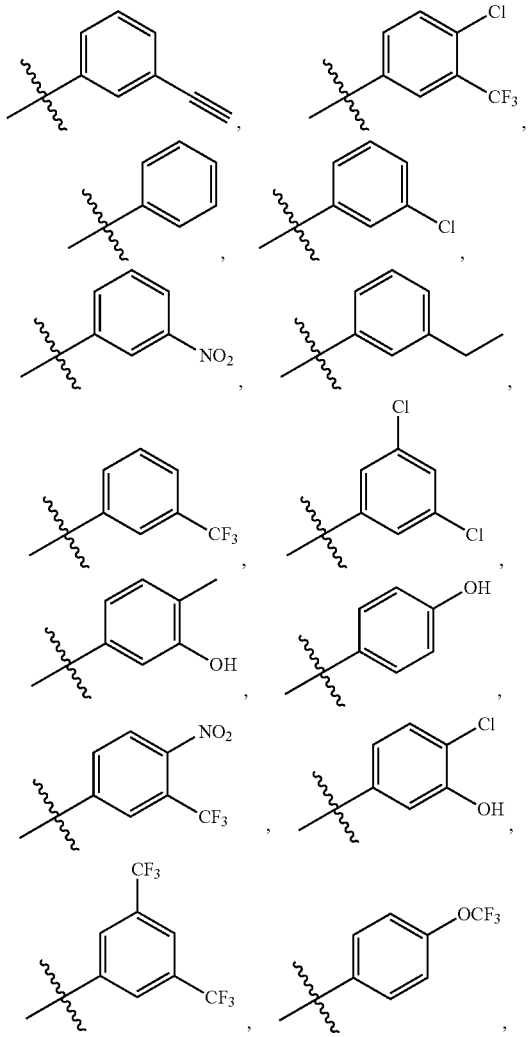

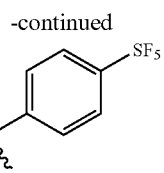

The general synthesis procedure of the pyrimidine derivatives is described as follow.

A solution of cyclopropane-1,1-dicarboxylic acid (1.0 mmol) and thionyl chloride (4 equilibrant) was heat for 16 hours. The resulting mixture was evaporated in rotavapor pump. The intermediate product was dissolve in THF and react with substituted-aniline. After the reaction was completed, the reaction mixture was washed with water, extracted with EtOAc, and the organic layer was dried over $MgSO_4$. After removal of $MgSO_4$ by filtration and evaporation of solvents, the crude residue was purified by chromatography on a silica gel column (silica gel columns 60, 0.063-0.200 mm or 0.040-0.063 mm, Merck; basic silica gel) using Ethyl actate/Hexane as eluent (33% to 45%) to give compounds (yield: 20-45%) below.

Embodiment 1: Synthesis of Di-Substituted SC5005 Derivatives

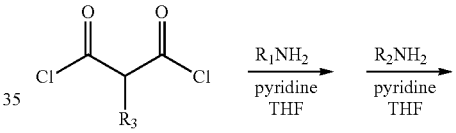

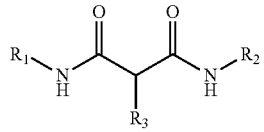

| Compound No | $R_1$ | $R_2$ | $R_3$ |
|---|---|---|---|
| SC5020 | 4-Cl-3-CF₃-phenyl | 4-Cl-3-CF₃-phenyl | cyclopropyl |
| SC5021 | 3-ethynyl-phenyl | 3-ethynyl-phenyl | cyclopropyl |
| SC5022 | phenyl | phenyl | 2-chloroethyl |

-continued

| Compound No | R$_1$ | R$_2$ | R$_3$ |
|---|---|---|---|
| SC5023 | 3-CF$_3$-phenyl | 3-CF$_3$-phenyl | -CH$_2$CH$_2$Cl |
| SC5024 | 4-OCF$_3$-phenyl | 4-OCF$_3$-phenyl | -CH$_2$CH$_2$Cl |
| SC5025 | 3,5-diCl-phenyl | 3,5-diCl-phenyl | -CH$_2$CH$_2$Cl |
| SC5026 | 3-ethynyl-phenyl | 3-ethynyl-phenyl | -CH$_2$CH$_2$Cl |
| SC5027 | 3-Cl-phenyl | 3-Cl-phenyl | -CH$_2$CH$_2$Cl |
| SC5028 | 3-NO$_2$-phenyl | 3-NO$_2$-phenyl | -CH$_2$CH$_2$Cl |
| SC5029 | 4-methyl-3-OH-phenyl | 4-methyl-3-OH-phenyl | -CH$_2$CH$_2$Cl |
| SC5030 | 4-Cl-3-OH-phenyl | 4-Cl-3-OH-phenyl | -CH$_2$CH$_2$Cl |
| SC5031 | 3-OH-phenyl | 3-OH-phenyl | -CH$_2$CH$_2$Cl |
| SC5032 | 3,5-diCF$_3$-phenyl | 3,5-diCF$_3$-phenyl | -CH$_2$CH$_2$Cl |

-continued

| Compound No | R₁ | R₂ | R₃ |
|---|---|---|---|
| SC5033 | 4-SF₅-phenyl | 4-SF₅-phenyl | -CH₂CH₂CH₂Cl |
| SC5034 | 4-NO₂-3-CF₃-phenyl | 4-NO₂-3-CF₃-phenyl | -CH₂CH₂CH₂Cl |
| SC5035 | 4-Cl-3-CF₃-phenyl | 3,5-diCl-phenyl | -CH₂CH₂CH₂Cl |
| SC5036 | 3,5-di(CF₃)-phenyl | 3,5-diCl-phenyl | -CH₂CH₂CH₂Cl |
| SC5037 | 4-Cl-3-CF₃-phenyl | 4-Cl-3-CF₃-phenyl | -CH₂CH=CH₂ |
| SC5038 | 3-ethynyl-phenyl | 3-ethynyl-phenyl | -CH₂CH=CH₂ |
| SC5039 | 3-ethyl-phenyl | 3-ethyl-phenyl | -CH₂CH=CH₂ |
| SC5040 | 3,5-diCl-phenyl | 3,5-diCl-phenyl | -CH₂CH=CH₂ |
| SC5041 | 4-NO₂-3-CF₃-phenyl | 3,5-diCl-phenyl | -CH₂CH₂CH₂Cl |

-continued

| Compound No | R₁ | R₂ | R₃ |
|---|---|---|---|
| SC5045 | 4-Cl-3-CF₃-phenyl | 4-Cl-3-CF₃-phenyl | -CH₂CH₂Cl |
| SC5046 | n-propyl | n-propyl | -CH₂CH₂Cl |
| SC5047 | n-butyl | n-butyl | -CH₂CH₂Cl |
| SC5048 | cyclohexyl | cyclohexyl | -CH₂CH₂Cl |
| SC5049 | 4-Cl-3-CF₃-phenyl | n-propyl | -CH₂CH₂Cl |
| SC5050 | 4-Cl-3-CF₃-phenyl | allyl | -CH₂CH₂Cl |
| SC5051 | allyl | allyl | -CH₂CH₂Cl |
| SC5052 | 4-Cl-3-CF₃-phenyl | n-butyl | -CH₂CH₂Cl |
| SC5053 | 4-Cl-3-CF₃-phenyl | cyclohexyl | -CH₂CH₂Cl |

The spectral data of the above compounds are listed below.

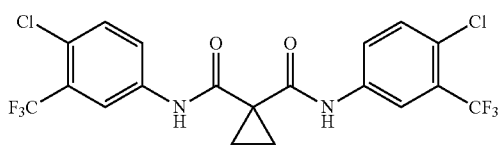 [SMILES: O=C(Nc1ccc(Cl)c(C(F)(F)F)c1)C1(C(=O)Nc2ccc(Cl)c(C(F)(F)F)c2)CC1]

N,N'-bis(4-chloro-3-(trifluoromethyl)phenyl)cyclopropane-1,1-dicarboxamide (5020)

$^1$H NMR (400 MHz, MeOD-d$_4$) δ 8.12 (d, J=2.8 Hz, 2H), 7.78 (dd, J=8.4, 2.8 Hz, 2H), 7.51 (d, J=8.4 Hz, 2H), 1.63 (s, 4H) ppm. $^{13}$C NMR (100 MHz, MeOD-d$_4$) δ 171.0, 138.9, 132.9, 129.2 (q, J=31.1 Hz), 127.5, 126.2, 124.1 (q, J=270.7 Hz), 120.8 (q, J=5.6 Hz), 31.8, 17.6 ppm. HRMS calculated for C$_{19}$H$_{12}$Cl$_2$F$_6$N$_2$O$_2$(M-H)$^-$: 483.0096. Found: 483.0102.

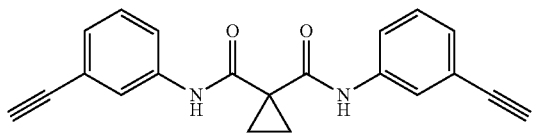 [SMILES: C#Cc1cccc(NC(=O)C2(C(=O)Nc3cccc(C#C)c3)CC2)c1]

N,N'-bis(3-ethynylphenyl)cyclopropane-1,1-dicarboxamide (5021)

$^1$H NMR (400 MHz, MeOD-d$_4$) δ 7.75 (s, 2H), 7.53 (d, J=8.0 Hz, 2H), 7.30 (t, J=8.0 Hz, 2H), 7.22 (d, J=8.0 Hz, 2H), 3.48 (s, 2H), 1.62 (s, 4H) ppm. HRMS calculated for C$_{21}$H$_{16}$N$_2$O$_2$ (M-H)$^-$: 327.1128. Found: 327.1131.

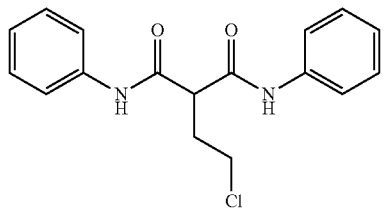 [SMILES: O=C(Nc1ccccc1)C(CCCl)C(=O)Nc1ccccc1]

2-(2-chloroethyl)-N$^1$,N$^3$-diphenylmalonamide (5022)

$^1$H NMR (400 MHz, MeOD-d$_4$) δ 7.58 (d, J=8.0 Hz, 4H), 7.32 (t, J=8.0 Hz, 4H), 7.12 (t, J=7.2 Hz, 2H), 3.75 (t, J=7.2 Hz, 1H), 3.69 (t, J=6.4 Hz, 2H), 2.48 (q, J=6.4 Hz, 2H) ppm. HRMS calculated for C$_{17}$H$_{17}$ClN$_2$O$_2$(M-H)$^-$: 315.0895. Found: 315.0906.

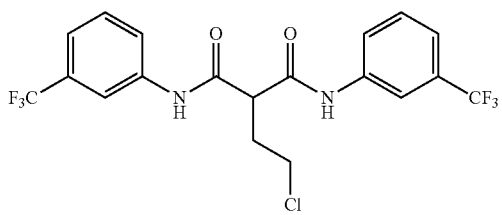 [SMILES: O=C(Nc1cccc(C(F)(F)F)c1)C(CCCl)C(=O)Nc1cccc(C(F)(F)F)c1]

2-(2-chloroethyl)-N$^1$,N$^3$-bis(3-(trifluoromethyl)phenyl)malonamide (5023)

$^1$H NMR (400 MHz, MeOD-d$_4$) δ 8.05 (s, 2H), 7.80 (d, J=8.0 Hz, 2H), 7.51 (t, J=8.0 Hz, 2H), 7.40 (d, J=8.0 Hz, 2H), 3.82 (t, J=7.2 Hz, 1H), 3.70 (t, J=6.8 Hz, 2H), 2.51 (q, J=6.8 Hz, 2H) ppm. $^{13}$C NMR (100 MHz, MeOD-d$_4$) δ 169.4, 140.3, 132.1 (q, J=32.0 Hz), 130.7, 125.4 (q, J=269.9 Hz), 124.5, 121.8 (d, J=3.6 Hz), 117.7 (d, J=3.9 Hz), 54.0, 43.2, 34.2 ppm. HRMS calculated for C$_{19}$H$_{15}$ClF$_6$N$_2$O$_2$ (M-H)$^-$: 451.0643. Found: 451.0658.

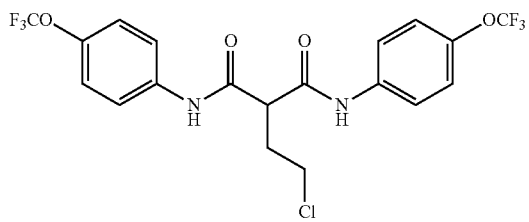 [SMILES: O=C(Nc1ccc(OC(F)(F)F)cc1)C(CCCl)C(=O)Nc1ccc(OC(F)(F)F)cc1]

2-(2-chloroethyl)-N$^1$,N$^3$-bis(4-(trifluoromethoxy)phenyl)malonamide (5024)

$^1$H NMR (400 MHz, MeOD-d$_4$) δ 7.68 (d, J=8.8 Hz, 4H), 7.22 (d, J=8.8 Hz, 4H), 3.79 (t, J=7.2 Hz, 1H), 3.68 (t, J=6.4 Hz, 2H), 2.48 (q, J=6.4 Hz, 2H) ppm. $^{13}$C NMR (100 MHz, MeOD-d$_4$) δ 169.2, 146.6, 138.4, 122.7, 122.6, 121.93 (q, J=253.6 Hz), 53.9, 43.2, 34.3 ppm. HRMS calculated for C$_{19}$H$_{15}$ClF$_6$N$_2$O$_4$(M-H)$^-$: 483.0541. Found: 483.0534.

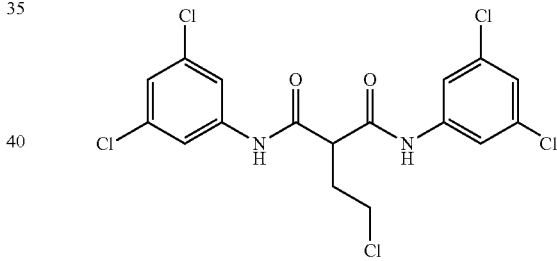

2-(2-chloroethyl)-N$^1$,N$^3$-bis(3,5-dichlorophenyl)malonamide (5025)

$^1$H NMR (400 MHz, MeOD-d$_4$) δ 7.65 (s, 4H), 7.17 (s, 2H), 3.76 (t, J=7.2 Hz, 1H), 3.68 (t, J=6.4 Hz, 2H), 2.46 (q, J=6.4 Hz, 2H) ppm. $^{13}$C NMR (100 MHz, DMSO-d$_6$) δ 167.1, 140.9, 134.1, 122.9, 117.6, 52.4, 42.9, 31.6 ppm. HRMS calculated for C$_{17}$H$_{13}$Cl$_5$N$_2$O$_2$ (M-H)$^-$: 450.9336. Found: 450.9354.

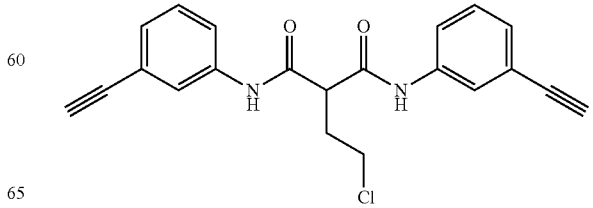

2-(2-chloroethyl)-N¹,N³-bis(3-ethynylphenyl)malonamide (5026)

¹H NMR (400 MHz, MeOD-d₄) δ 7.75 (s, 2H), 7.58 (d, J=7.6 Hz, 2H), 7.30 (t, J=7.6 Hz, 2H), 7.21 (d, J=7.6 Hz, 2H), 3.76 (t, J=7.6 Hz, 1H), 3.68 (t, J=6.8 Hz, 2H), 3.48 (s, 2H), 2.47 (q, J=6.8 Hz, 2H) ppm. ¹³C NMR (100 MHz, MeOD-d₄) δ 169.2, 139.5, 130.0, 129.0, 124.6, 124.2, 121.8, 84.0, 78.8, 53.9, 43.2, 34.2 ppm. HRMS calculated for $C_{21}H_{17}ClN_2O_2$(M-H)⁻: 363.0895. Found: 363.0892.

2-(2-chloroethyl)-N¹,N³-bis(3-hydroxy-4-methylphenyl)malonamide (5029)

¹H NMR (400 MHz, MeOD-d₄) δ 7.15 (d, J=2.0 Hz, 2H), 7.01 (d, J=8.0 Hz, 2H), 6.84 (dd, J=8.0, 2.0 Hz, 2H), 3.74 (t, J=7.6 Hz, 2H), 2.87 (t, J=7.6 Hz, 2H), 2.14 (s, 6H) ppm.

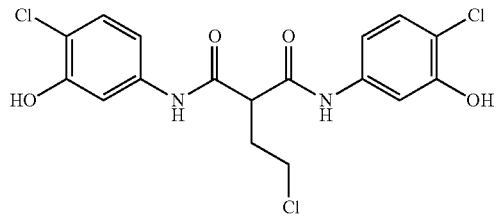

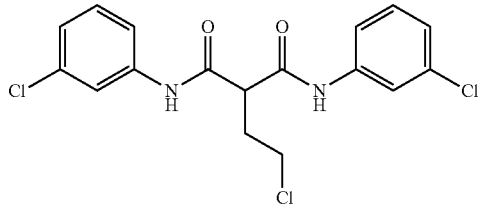 [SMILES: O=C(Nc1cccc(Cl)c1)C(CCCl)C(=O)Nc1cccc(Cl)c1]

N¹,N³-bis(4-chloro-3-hydroxyphenyl)-2-(2-chloroethyl)malonamide (5030)

¹H NMR (400 MHz, MeOD-d₄) δ 7.41 (s, 2H), 7.21 (d, J=8.8 Hz, 2H), 6.93 (d, J=8.8 Hz, 2H), 3.72-3.65 (m, 3H), 2.44 (q, J=6.8 Hz, 2H) ppm.

2-(2-chloroethyl)-N¹,N³-bis(3-chlorophenyl)malonamide (5027)

¹H NMR (400 MHz, MeOD-d₄) δ 7.77 (s, 2H), 7.45 (d, J=8.4 Hz, 2H), 7.29 (t, J=8.4 Hz, 2H), 7.11 (d, J=8.4 Hz, 2H), 3.76 (t, J=7.2 Hz, 1H), 3.68 (t, J=6.8 Hz, 2H), 2.47 (q, J=6.8 Hz, 2H) ppm. ¹³C NMR (100 MHz, MeOD-d₄) δ 169.2, 140.8, 135.4, 131.1, 125.4, 121.2, 119.4, 54.0, 43.2, 34.2 ppm. HRMS calculated for $C_{17}H_{15}Cl_3N_2O_2$ (M-H)⁻: 383.0115. Found: 383.0114.

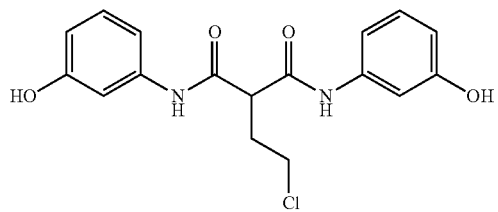 [SMILES: O=C(Nc1cccc(O)c1)C(CCCl)C(=O)Nc1cccc(O)c1]

2-(2-chloroethyl)-N¹,N³-bis(3-hydroxyphenyl)malonamide (5031)

¹H NMR (400 MHz, MeOD-d₄) δ 7.18 (s, 2H), 7.11 (t, J=8.0 Hz, 2H), 6.96 (d, J=8.0 Hz, 2H), 6.55 (d, J=8.0 Hz, 2H), 3.72-3.65 (m, 3H), 2.45 (q, J=6.8 Hz, 2H) ppm.

2-(2-chloroethyl)-N¹,N³-bis(3-nitrophenyl)malonamide (5028)

¹H NMR (400 MHz, MeOD-d₄) δ 8.63 (s, 2H), 8.02 (t, J=8.0 Hz, 4H), 7.60 (t, J=8.0 Hz, 2H), 3.82 (t, J=7.6 Hz, 2H), 2.94 (t, J=7.6 Hz, 2H) ppm. ¹³C NMR (100 MHz, MeOD-d₄) δ 166.9, 149.8, 140.3, 130.9, 127.7, 120.4, 116.6, 72.0, 42.4, 40.2 ppm.

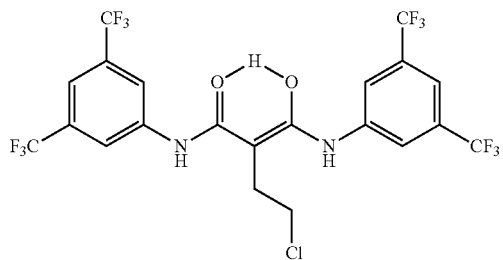

N,N³-bis(3,5-bis(trifluoromethyl)phenyl)-2-(2-chloroethyl)malonamide (5032)

¹H NMR (400 MHz, MeOD-d₄) δ 8.30 (s, 4H), 7.72 (s, 2H), 3.82 (t, J=7.6 Hz, 2H), 2.94 (t, J=7.6 Hz, 2H) ppm. ¹³C NMR (100 MHz, MeOD-d₄) δ 167.1, 141.1, 133.3 (q, J=33.2 Hz), 124.6 (q, J=270.2 Hz), 121.7, 118.8 (q, J=3.5 Hz), 71.8, 42.3, 40.1 ppm.

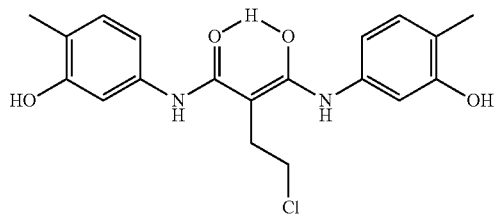

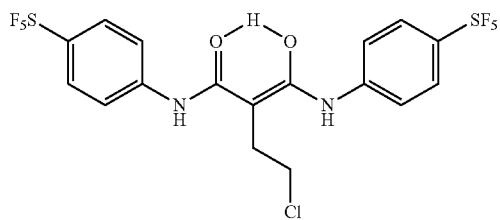

N¹,N³-bis(4-pentafluorosulfurphenyl)-2-(2-chloro-ethyl)malonamide (5033)

¹H NMR (400 MHz, DMSO-d₆) δ 7.91-7.88 (m, 8H), 3.77 (t, J=7.2 Hz, 2H), 2.88 (t, J=7.2 Hz, 2H) ppm. ¹³C NMR (100 MHz, DMSO-d₆) δ 165.0, 148.1 (q, J=16.1 Hz), 141.4, 126.6, 120.5, 71.1, 40.3 ppm.

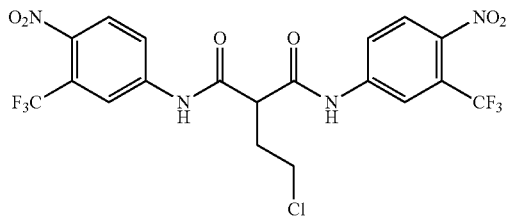 [SMILES: O=C(Nc1ccc([N+](=O)[O-])c(C(F)(F)F)c1)C(CCCl)C(=O)Nc1ccc([N+](=O)[O-])c(C(F)(F)F)c1]

2-(2-chloroethyl)-N¹,N³-bis(4-nitro-3-(trifluoromethyl)phenyl)malonamide (5034)

¹H NMR (400 MHz, MeOD-d₄) δ 8.26 (s, 2H), 8.09-8.04 (m, 4H), 3.90 (t, J=6.8 Hz, 1H), 3.73 (t, J=6.4 Hz, 2H), 2.53 (q, J=6.4 Hz, 2H) ppm.

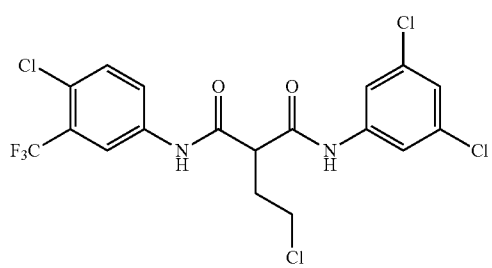 [SMILES: O=C(Nc1cc(Cl)cc(Cl)c1)C(CCCl)C(=O)Nc1ccc(Cl)c(C(F)(F)F)c1]

N¹-(4-chloro-3-(trifluoromethyl)phenyl)-2-(2-chloroethyl)-N³-(3,5-dichlorophenyl)malonamide (5035)

¹H NMR (400 MHz, MeOD-d₄) δ 8.13 (s, 1H), 7.83 (d, J=8.8 Hz, 1H), 7.65 (s, 2H), 7.55 (d, J=8.8 Hz, 1H), 7.17 (s, 1H), 3.78 (t, J=7.6 Hz, 1H), 3.69 (t, J=6.4 Hz, 2H), 2.48 (q, J=6.4 Hz, 2H) ppm. ¹³C NMR (100 MHz, MeOD-d₄) δ 169.3, 169.2, 141.7, 138.8, 136.1, 133.0, 129.3 (q, J=31.3 Hz), 127.5, 125.5, 124.9, 124.1 (q, J=270.4 Hz), 120.0 (q, J=5.5 Hz), 119.3, 54.1, 43.2, 34.0 ppm.

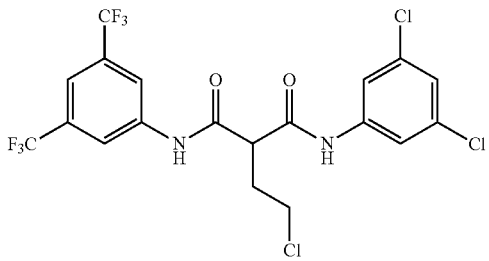 [SMILES: O=C(Nc1cc(Cl)cc(Cl)c1)C(CCCl)C(=O)Nc1cc(C(F)(F)F)cc(C(F)(F)F)c1]

N¹-(3,5-bis(trifluoromethyl)phenyl)-2-(2-chloro-ethyl)-N³-(3,5-dichlorophenyl) malonamide (5036)

¹H NMR (400 MHz, MeOD-d₄) δ 8.25 (s, 2H), 7.67 (s, 1H), 7.65 (s, 2H), 7.16 (s, 1H), 3.82 (t, J=6.8 Hz, 1H), 3.70 (t, J=6.4 Hz, 2H), 2.50 (q, J=6.4 Hz, 2H) ppm.

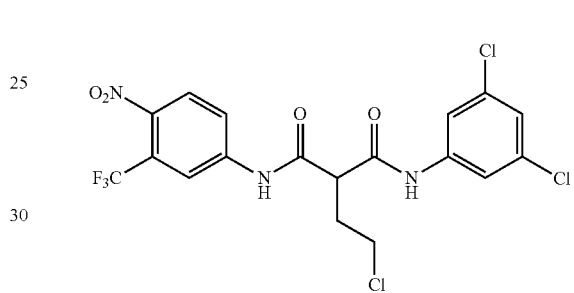

2-(2-chloroethyl)-N¹-(3,5-dichlorophenyl)-N³-(4-nitro-3-(trifluoromethyl)phenyl)malonamide (5041)

¹H NMR (400 MHz, MeOD-d₄) δ 8.24 (s, 1H), 8.04 (q, J=8.8 Hz, 2H), 7.63 (s, 2H), 7.14 (s, 1H), 3.85 (t, J=6.8 Hz, 1H), 3.70 (t, J=6.8 Hz, 2H), 2.49 (q, J=6.8 Hz, 2H) ppm.

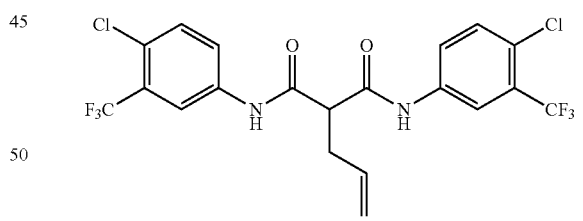

2-allyl-N¹,N³-bis(4-chloro-3-(trifluoromethyl)phenyl)malonamide (5037)

¹H NMR (400 MHz, CDCl₃-d₁) δ 9.08 (s, 2H), 7.93 (s, 2H), 7.67 (d, J=8.4 Hz, 2H), 7.45 (d, J=8.4 Hz, 2H), 5.81-5.73 (m, 1H), 5.19 (d, J=16.8 Hz, 1H), 5.12 (d, J=9.6 Hz, 1H), 3.39 (t, J=7.6 Hz, 1H), 2.79 (t, J=7.6 Hz, 2H) ppm. ¹³C NMR (100 MHz, MeOD-d₄) δ 169.9, 138.8, 135.4, 133.0, 129.3 (q, J=31.1 Hz), 127.4, 125.5, 124.1 (q, J=270.7 Hz), 120.0 (q, J=5.4 Hz), 118.3, 56.4, 35.9 ppm.

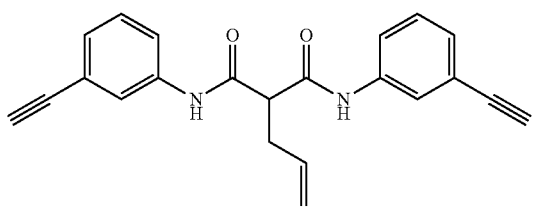 [SMILES: C#Cc1cccc(NC(=O)C(CC=C)C(=O)Nc2cccc(C#C)c2)c1]

2-allyl-N[1],N[3]-bis(3-ethynylphenyl)malonamide (5038)

$^1$H NMR (400 MHz, MeOD-d$_4$) δ 7.74 (s, 2H), 7.55 (d, J=7.6 Hz, 2H), 7.28 (t, J=7.6 Hz, 2H), 7.20 (d, J=7.6 Hz, 2H), 5.93-5.83 (m, 1H), 5.18 (d, J=17.2 Hz, 1H), 5.08 (d, J=10.4 Hz, 1H), 3.54 (t, J=7.2 Hz, 1H), 3.47 (s, 2H), 2.77 (t, J=7.2 Hz, 2H) ppm. $^{13}$C NMR (100 MHz, MeOD-d$_4$) δ 169.9, 139.5, 135.5, 130.0, 129.0, 124.6, 124.2, 121.8, 118.2, 84.0, 78.8, 56.2, 36.3 ppm.

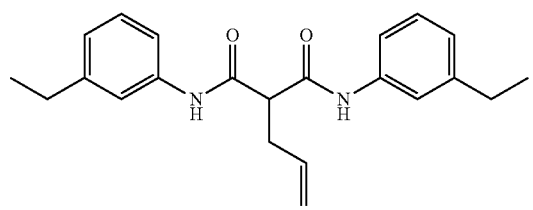 [SMILES: C=CCC(C(=O)Nc1cccc(CC)c1)C(=O)Nc1cccc(CC)c1]

2-allyl-N[1],N[3]-bis(3-ethylphenyl)malonamide (5039)

$^1$H NMR (400 MHz, CDCl$_3$-d$_1$) δ 8.83 (s, 2H), 7.37 (d, J=7.6 Hz, 2H), 7.36 (s, 2H), 7.21 (t, J=7.6 Hz, 2H), 6.96 (d, J=7.6 Hz, 2H), 5.87-5.79 (m, 1H), 5.18 (d, J=16.8 Hz, 1H), 5.08 (d, J=10.4 Hz, 1H), 3.39 (t, J=7.2 Hz, 1H), 2.79 (t, J=7.2 Hz, 2H), 2.61 (q, J=7.6 Hz, 4H), 1.20 (t, J=7.6 Hz, 6H) ppm.

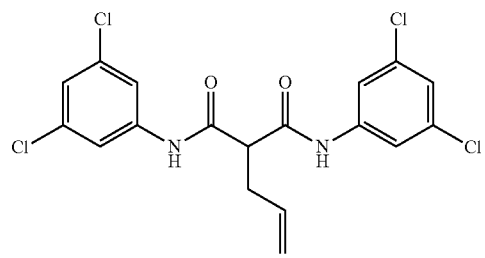 [SMILES: C=CCC(C(=O)Nc1cc(Cl)cc(Cl)c1)C(=O)Nc1cc(Cl)cc(Cl)c1]

2-allyl-N[1],N[3]-bis(3,5-dichlorophenyl)malonamide (5040)

$^1$H NMR (400 MHz, CDCl$_3$-d$_1$) b 8.86 (s, 2H), 7.50 (d, J=1.6 Hz, 4H), 7.13 (t, J=1.6 Hz, 2H), 5.81-5.73 (m, 1H), 5.20 (d, J=17.2 Hz, 1H), 5.14 (d, J=10.4 Hz, 1H), 3.35 (t, J=7.2 Hz, 1H), 2.77 (t, J=7.2 Hz, 2H) ppm.

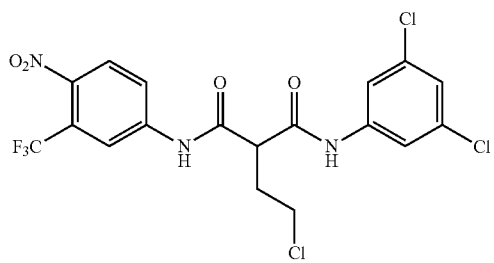 [SMILES: O=C(Nc1cc(Cl)cc(Cl)c1)C(CCCl)C(=O)Nc1ccc([N+](=O)[O-])c(C(F)(F)F)c1]

2-(2-chloroethyl)-N[1]-(3,5-dichlorophenyl)-N[3]-(4-nitro-3-(trifluoromethyl)phenyl)malonamide (5041)

$^1$H NMR (400 MHz, CD$_3$OD) δ 8.24 (s, 1H), 8.04 (dd, 14.2 Hz, 8.8 Hz, 2H), 7.63 (s, 2H), 7.14 (s, 1H), 3.85 (t, 6.8 Hz, 1H), 3.70 (t, 6.4 Hz, 2H), 2.49 (q, 6.8 Hz, 2H) ppm.

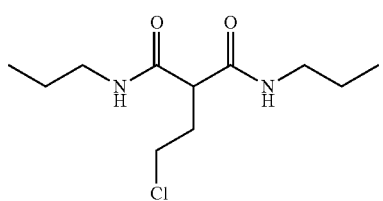 [SMILES: CCCNC(=O)C(CCCl)C(=O)NCCC]

2-(2-chloroethyl)-N1,N3-dipropylmalonamide (5046)

$^1$H NMR (400 MHz, CDCl$_3$): δ 6.89 (brs, 2H), 3.57 (t, J=8.8 Hz, 2H), 3.30 (t, J=10 Hz, 1H), 3.26-3.20 (m, 4H), 2.32 (q, J=8.8 Hz, 2H), 1.61-1.49 (m, 4H), 0.93 (t, J=9.6 Hz, 6H); $^{13}$C NMR (100 MHz, CDCl$_3$-d$_1$): δ 170.1, 52.3, 42.6, 41.6, 35.1, 22.8, 11.5 ppm.

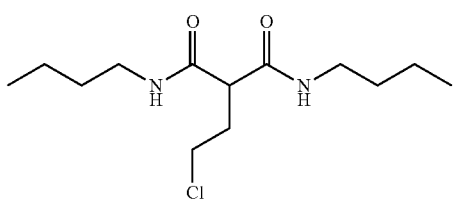 [SMILES: CCCCNC(=O)C(CCCl)C(=O)NCCCC]

N1,N3-dibutyl-2-(2-chloroethyl)malonamide (5047)

$^1$H NMR (400 MHz, CDCl$_3$): δ 6.92 (brs, 2H), 3.54 (t, J=8.4 Hz, 2H), 3.30-3.21 (m, 5H), 2.29 (q, J=8.4 Hz, 2H), 1.51-1.44 (m, 4H), 1.39-1.27 (m, 4H), 0.91 (t, J=9.6 Hz, 6H); $^{13}$C NMR (100 MHz, CDCl$_3$-d$_1$): δ 170.1, 52.2, 42.6, 39.6, 35.1, 31.6, 20.2, 13.9 ppm.

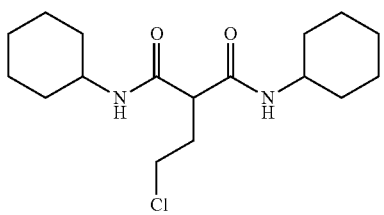 [SMILES: O=C(NC1CCCCC1)C(CCCl)C(=O)NC1CCCCC1]

2-(2-chloroethyl)-N1,N3-dicyclohexylmalonamide (5048)

¹H NMR (400 MHz, CDCl₃): δ 6.61 (d, J=10.4 Hz, 2H), 3.79-3.67 (m, 2H), 3.55 (t, J=8.4 Hz, 2H), 3.18 (t, J=10.4 Hz, 1H), 2.28 (q, J=8.4 Hz, 2H), 1.89-1.84 (m, 4H), 1.72-1.56 (m, 9H), 1.42-1.29 (m, 4H), 1.24-1.10 (m, 6H); ¹³C NMR (100 MHz, CDCl₃-d₁): δ 169.2, 52.4, 48.6, 42.7, 35.1, 32.9, 25.7, 24.9 ppm.

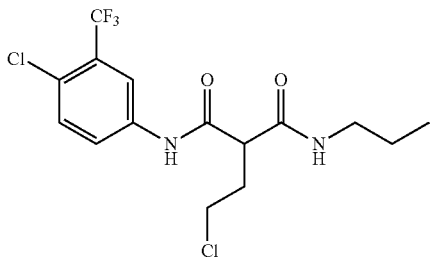 [SMILES: CCCNC(=O)C(CCCl)C(=O)Nc1ccc(Cl)c(C(F)(F)F)c1]

N1-(4-chloro-3-(trifluoromethyl)phenyl)-2-(2-chloroethyl)-N3-propylmalonamide (5049)

¹H NMR (400 MHz, DMSO): δ 10.41 (s, 1H), 8.17 (d, J=3.2 Hz, 1H), 7.93 (t, J=7.2 Hz, 1H), 7.82 (dd, J=12, 3.2 Hz, 1H), 7.65 (d, J=12 Hz, 1H), 3.60 (t, J=9.2 Hz, 2H), 3.50 (t, J=9.6 Hz, 1H), 3.11-2.94 (m, 2H), 2.24 (q, J=9.2 Hz, 2H), 1.46-1.34 (m, 2H), 0.80 (t, J=9.6 Hz, 3H); ¹³C NMR (100 MHz, DMSO-d₆): δ 168.5, 168.0, 139.0, 132.8, 128.8, 127.4 (q, J=41 Hz), 125.2, 124.8, 121.6, 118.7, 43.8, 41.3, 32.4, 22.8, 11.9 ppm.

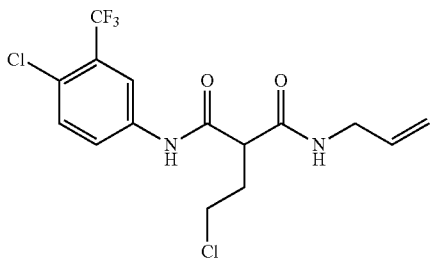 [SMILES: C=CCNC(=O)C(CCCl)C(=O)Nc1ccc(Cl)c(C(F)(F)F)c1]

N1-allyl-N3-(4-chloro-3-(trifluoromethyl)phenyl)-2-(2-chloroethyl)malonamide (5050)

1H NMR (400 MHz, DMSO): δ 10.49 (s, 1H), 8.18 (d, J=3.2 Hz, 1H), 8.14 (t, J=8 Hz, 1H), 7.83 (dd, J=12, 3.2 Hz, 1H), 7.65 (d, J=12 Hz, 1H), 5.84-5.71 (m, 1H), 5.13-4.99 (m, 2H), 3.74-3.68 (m, 2H), 3.63-3.55 (m, 3H), 2.26 (q, J=9.6 Hz, 2H) ppm.

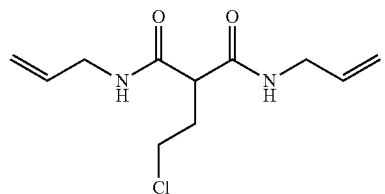 [SMILES: C=CCNC(=O)C(CCCl)C(=O)NCC=C]

N1,N3-diallyl-2-(2-chloroethyl)malonamide (5051)

1H NMR (400 MHz, DMSO): δ 8.00 (t, J=7.2 Hz, 2H), 5.83-5.71 (m, 2H), 5.13-5.01 (m, 4H), 3.72-3.67 (m, 4H), 3.52 (t, J=8.8 Hz, 2H), 3.36 (t, J=9.6 Hz, 1H), 2.13 (q, J=8.8 Hz, 2H); 13C NMR (100 MHz, DMSO-d6): δ 168.7, 135.7, 115.7, 50.9, 43.9, 41.7, 32.7 ppm.

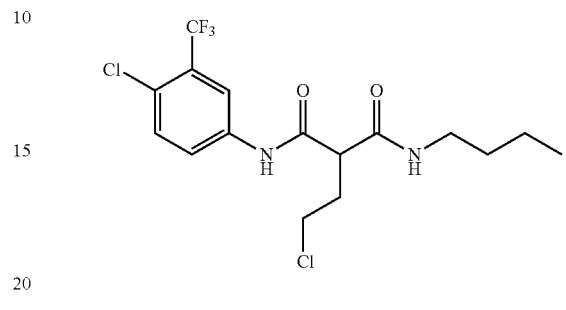

N1-butyl-N3-(4-chloro-3-(trifluoromethyl)phenyl)-2-(2-chloroethyl)malonamide (5052)

¹H NMR (400 MHz, DMSO): δ 10.40 (s, 1H), 8.16 (d, J=3.6 Hz, 1H), 7.91 (t, J=7.6 Hz, 1H), 7.82 (dd, J=11.6, 3.6 Hz, 1H), 7.66 (d, J=11.6 Hz, 1H), 3.59 (t, J=9.2 Hz, 2H), 3.49 (t, J=9.6 Hz, 1H), 3.10-3.02 (m, 2H), 2.23 (q, J=9.2 Hz, 2H), 1.39-1.32 (m, 2H), 1.26-1.19 (m, 2H), 0.81 (t, J=9.6 Hz, 3H) ppm.

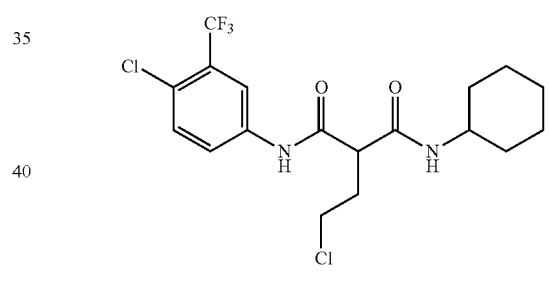

N1-(4-chloro-3-(trifluoromethyl)phenyl)-2-(2-chloroethyl)-N3-cyclohexylmalonamide (5053)

¹H NMR (400 MHz, DMSO): δ 10.37 (s, 1H), 8.18 (d, J=3.2 Hz, 1H), 7.85-7.81 (m, 2H), 7.67 (d, J=11.6 Hz, 1H), 3.60 (t, J=9.2 Hz, 2H), 3.49 (t, J=9.2 Hz, 2H), 2.24 (q, J=9.2 Hz, 2H), 1.76-1.66 (m, 4H), 1.53 (brs, 1H), 1.28-1.09 (m, 5H); ¹³C NMR (100 MHz, DMSO-d₆): δ 167.8, 166.4, 138.3, 132.2, 126.7 (q, J=40.3 Hz), 124.5, 124.1, 120.9, 117.9 (q, J=7.3 Hz), 51.4, 47.9, 43.2, 32.2, 32.0, 31.7, 25.2, 24.4 ppm.

Structure of SC78

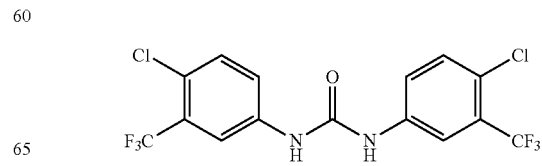

Pharmaceutical Composition and Medical Application Thereof

In one aspect, the present invention directs to a pharmaceutical composition.

The pharmaceutical composition comprises an effective amount of a compound having a chemical structure (I) below and a pharmaceutically acceptable carrier.

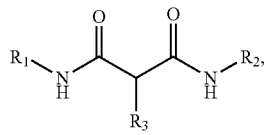

(I)

In another aspect, the present invention directs to a method of bacterial cell killing. The method comprises contacting a cell with an effective amount of a compound having the chemical structure (I) above.

In yet another aspect, the present invention directs to a method of treating bacteria. The method comprises administrating an effective amount of a compound having a chemical structure (I) above by a needed subject. The bacteria above can be a Staphylococcus aureus strains ATCC 12598, ATCC 29213, NCTC 8325, methicillin-resistant Staphylococcus aureus (MRSA) strains ATCC 33592, ATCC 49476, a clinically isolated MRSA strain carrying SCCmec $V_T$,[26] one hundred clinically isolated MRSA strains, a vanA-mediated vancomycin-resistant Staphylococcus aureus (VRSA) strain (SJC1200), and a clinical isolated vancomycin-intermediate Staphylococcus aureus (VISA) strain, S. epidermidis strains ATCC 35984 and ATCC 12228, S. haemolyticus strain ATCC 29970, S. hominis strain ATCC 27844, S. intermedius strain ATCC 29663, S. saprophyticus strain ATCC 15305, a clinically isolated S. lugdunesis, Enterococcus faecalis ATCC 19433, Enterococcus faecium ATCC 35667, Enterococcus faecium ATCC 19434, Bacillus cereus ATCC 11778, Bacillus subtilis BCRC 10255, Corynebacterium diphtheria ATCC 11913, Listeria monocytogenes ATCC 19113, Erysipelothrix rhusiopathiae ATCC 19414, Streptococcus pyogenes ATCC 19615, Escherichia coli ATCC 25922, Salmonella Typhimurium ATCC 14028, Acinetobacter baumannii BCRC 80276, a clinically isolated S. lugdunesis, and Vancomycin-Resistant Enterococcus faecium (VR-E).

Identification of Potent Malonamide Derivatives

To exploit the antibacterial activity of malonate derivatives, S. aureus and S. epidermidis were used as representatives in the drug screening. A library consisting of 73 malonamide derivatives were screened for growth inhibitory activities against S. aureus (NCTC 8325) and S. epidermidis (ATCC 35984). Of these derivatives, compound SC5005 and it derivatives exhibited potent anti-Staphylococcus activity with MICs≤1 mg/L for S. aureus and S. epidermidis strains tested (Table 1). These new agents also possess potent inhibitory activity against MRSA strains tested, with MICs same as that against methicillin-sensitive S. aureus (MSSA) strains (Table 1). As these MRSA strains have been reported to possess resistance to different classes of antibiotics, this finding suggests that a novel antibacterial target might be involved in the mechanism of action of these agents.

TABLE 1

Antibacterial activity of test agents against S. aureus, S. epidermidis and MRSA.

| | MIC (mg/L) | | | | | | |
|---|---|---|---|---|---|---|---|
| Compound | S. aureus NCTC 8325 | S. aureus ATCC 12598 | S. epidermidis ATCC 12228 | S. epidermidis ATCC 35984 | MRSA ATCC 33592 | MRSA ATCC 49476 | MRSA SCCmec $V_T$ |
| SC78 | 0.25 | 0.25 | 0.25 | 0.25 | 0.25 | 025 | 0.25 |
| SC5005 | 0.5 | 0.5 | 0.5 | 0.5 | 0.5 | 0.5 | 0.5 |
| Ampicillin | 0.25 | — | 32 | >32 | >64 | >64 | 64 |
| Chloramphenicol | 4 | — | 2 | — | 32 | 8 | 64 |
| Erythromycin | 0.5 | — | 4 | 4 | >64 | >64 | >64 |
| Ofloxacin | 0.125 | — | 0.25 | — | 0.25 | 0.5 | 0.25 |
| Rifampicin | 0.125 | — | <0.004 | — | >64 | 0.25 | 0.5 |
| Tetracycline | 0.125 | — | 8 | 0.25 | >64 | >64 | 32 |
| Vancomycin | 0.5 | — | 1 | — | 1 | 1 | 1 |

In addition to the antibacterial activities, the cytotoxic effects of these malonate derivatives on human cancer cell lines were also assessed. Among these new agents, only compound SC5005 had a lower antiproliferative potency against all human cancer cells with the $IC_{50}$ ranging from 15 to 20 mg/L, resulting in a selectivity ratios of up to 40 (Table 2).

TABLE 2

Anti-Staphylococcus (MIC) versus antiproliferative ($IC_{50}$) activities of test agents.

| | S. aureus NCTC 8325 | HEK-293 | | K-562 | | HT-29 | |
|---|---|---|---|---|---|---|---|
| Compound | MIC (μg/ml) | $IC_{50}$ (μg/ml) | Selectivity ratio[a] | $IC_{50}$ (μg/ml) | Selectivity ratio | $IC_{50}$ (μg/ml) | Selectivity ratio |
| SC72 | 1 | 2.76 | 2.76 | 5.94 | 5.94 | — | — |
| SC78 | 0.25 | 1.13 | 4.52 | 4.73 | 18.92 | 4.51 | 18.04 |
| SC79 | 0.5 | 2.22 | 4.44 | 1.78 | 3.56 | — | — |

TABLE 2-continued

Anti-*Staphylococcus* (MIC) versus antiproliferative (IC$_{50}$) activities of test agents.

| Compound | S. aureus NCTC 8325 MIC (µg/ml) | HEK-293 IC$_{50}$ (µg/ml) | HEK-293 Selectivity ratio[a] | K-562 IC$_{50}$ (µg/ml) | K-562 Selectivity ratio | HT-29 IC$_{50}$ (µg/ml) | HT-29 Selectivity ratio |
|---|---|---|---|---|---|---|---|
| SC80 | 0.5 | 2.12 | 4.24 | 4.12 | 8.24 | 4.60 | 9.2 |
| SC5005 | 0.5 | 16.79 | 33.58 | 20.23 | 40.46 | 14.56 | 29.12 |

[a]Selectivity ratio = IC$_{50}$/MIC against *S. aureus*

Antibacterial Spectra of Compounds SC78 and SC5005 Against Different *Staphylococcus* Species and Clinical Isolated MRSAs SC78 and SC5005 were tested in a panel of representative *Staphylococcus* pathogens, consisting of strains of *S. aureus*, *S. epidermidis S. haemolyticus*, *S. hominis*, *S. intermedius*, *S. saprophyticus*, and *S. lugdunesis*. As shown in Table 3, with the exception of *S. intermedius*, and *S. haemolyticus* showed a lesser degree of susceptibility, the inhibitory potencies of compound SC78 and SC5005 against these *Staphylococcus* species were consistent with those of *S. aureus* and *S. epidermidis*.

TABLE 3

Antibacterial activity SC78 and SC5005 against *Staphylococcus* pathogens, VISA, VRSA and clinical isolated MRSAs.

| *Staphylococcus* species | MIC (mg/L) SC78 | SC5005 | Vancomycin |
|---|---|---|---|
| *S. aureus* (NCTC 8325) | 0.25 | 0.5 | 0.5 |
| *S. epidermidis* (ATCC 35984) | 0.25 | 0.5 | — |
| *S. haemolyticus* (ATCC 29970) | 0.5 | 1 | — |
| *S. hominis* (ATCC 27844) | 0.25 | 0.25 | — |
| *S. intermedius* (ATCC 29663) | 1 | 1 | — |
| *S. saprophyticus* (ATCC 15305) | 0.25 | 0.5 | — |
| *S. lugdunesis* (NTUH isolate) | 0.25 | 0.5 | — |
| VISA | 0.25 | 0.5 | 4 |
| VRSA (SJC1200) | 0.25 | 0.5 | 512 |
| Clinical isolated MRSAs[a] | 0.25 | 0.5[b] | — |

[a]A total of one hundred clinical isolated MRSA from NTUH was tested.
[b]The value represented the MIC$_{90}$ against MRSA isolates tested.

To further investigate the potency of SC78 and SC5005 against MRSAs, a total of one hundred clinical isolated MRSA strains from the National Taiwan University Hospital, which have been identified to carry type II, III, IV or V$_T$ of SCCmec, were assessed for their susceptibility to these two agents. As result shown, the MIC$_{90}$ of SC78 and SC5005, defined as the concentration that inhibits 90% of bacteria strains tested, against these clinical isolated MRSA strains were 0.25 mg/L and 0.5 mg/L, respectively, which were consistent with the MICs against reference strains of *S. aureus*, *S. epidermidis* and MRSA (Table 3).

Antibacterial Activity of Compounds SC78 and SC5005 Against VISA and VRSA

After being introduced in 1958, vancomycin has always been the last line of defence for the treatment of MRSA infection. However, in the early 2000s, the emergence of vancomycin intermediate-susceptible *S. aureus* (VISA) and vancomycin-resistant *S. aureus* (VRSA) has been reported. The decrease of *S. aureus*' susceptibility to vancomycin has increased the difficulty of treatment and highlights an urgent need of novel therapeutic agents for VISA and VRSA infection. To examine whether the antibacterial activities of SC78 and SC5005 are able to suppress the growth of VISA and VRSA, the susceptibility of a clinical isolated VISA strain and a vanA-mediated VRSA strain (SJC1200) to these two agents and vancomycin were assayed. As result shown in table 3, the VISA strain showed a moderate decrease in the susceptibility to vancomycin, as demonstrated by a 4-fold increase in the value of MIC comparing to that of vancomycin-susceptible *S. aureus* (VSSA), including MRSA (ATCC 33592), MRSA (ATCC 49476) and MRSA (SCCmec VT). In contrast, the VRSA strain was highly resistant to vancomycin with an over five-hundred decrease in the susceptibility to vancomycin. Though these two strains exhibited different resistance to vancomycin, their susceptibility to SC78 and SC5005 were consistent with the VSSA strain, suggesting that the antibacterial mechanism of these two malonamide derived agents is different from that of vancomycin. The findings above highlighted the potential of these malonamide derivatives in treatment of infection caused by *S. aureus* strains with resistance to multiple antibiotics, including vancomycin.

Antibacterial Spectra of SC78 and SC5005 Against Different Pathogenic Gram-Positive Bacteria, Gram-Negative Bacteria and Mycobacteria To further investigate whether these two agents can suppress Gram-positive bacteria other than *Staphylococcus*, the activity of SC78 and SC5005 against a panel of Gram-positive bacteria, including *Enterococcus faecalis* (ATCC 19433), *Enterococcus faecium* (ATCC 35667 & ATCC 19434), clinically-isolated vancomycin resistant *Enterococcus faecium* (VR-E), *Bacillus cereus* (ATCC 11778), *Bacillus subtilis* (BCRC 10255), *Corynebacterium diphtheriae* (ATCC 11913), *Listeria monocytogenes* (ATCC 19113), *Erysipelothrix rhusiopathiae* (ATCC 19414), *Streptococcus pyogenes* (ATCC 19615), *Clostridium difficile* (630 & R$_{20291}$) was evaluated. As the results shown in table 4, SC78 and SC5005 can suppress all Gram-positive bacteria tested with the MICs same as that against *S. aureus*. These results indicated that SC78 and SC5005 possess broad-spectrum antibacterial activities on Gram-positive bacteria. Moreover, SC78 and SC5005 also possess suppressive effects on *Mycobacterium tuberculosis* (H37Ra) with MIC of 1 mg/L and 16 mg/L, respectively, indicating that these two agents are effective against *Mycobacterium* species.

TABLE 4

Antibacterial activity of SC78 and SC5005 against Gram-positive bacteria, Gram-negative bacteria and Mycobacteria.

| Bacteria | MIC (mg/L) SC78 | SC5005 |
|---|---|---|
| Gram-positive bacteria | | |
| *Enterococcus faecalis* ATCC 19433 | 0.25 | 0.5 |
| *Enterococcus faecium* ATCC 35667 | 0.25 | 0.5 |

TABLE 4-continued

Antibacterial activity of SC78 and SC5005 against Gram-positive bacteria, Gram-negative bacteria and Mycobacteria.

| Bacteria | MIC (mg/L) | |
|---|---|---|
| | SC78 | SC5005 |
| Enterococcus faecium ATCC 19434 | 0.5 | 1 |
| VR-E. faecium | 0.25 | 0.5 |
| Bacillus cereus ATCC 11778 | 0.25 | 0.5 |
| Bacillus subtilis BCRC 10255 | 0.25 | 0.5 |
| Corynebacterium diphtheriae ATCC 11913 | 0.25 | 0.5 |
| Listeria monocytogenes ATCC 19113 | 0.0625 | 0.125 |
| Streptococcus pyogenes ATCC 19615 | 0.25 | 0.5 |
| Clostridium difficile 630[a] | 0.5 | 0.5 |
| Clostridium difficile R20291[a] | 0.25 | 0.5 |
| Gram-negative bacteria | | |
| Escherichia coli ATCC 25922 | >64 | >64 |
| Salmonella Typhimurium ATCC 14028 | >64 | >64 |
| Acinetobacter baumannii BCRC 80276 | >64 | >64 |
| Mycobacteria | | |
| Mycobacterium tuberculosis H37Ra | 1 | 16 |

In addition to Gram-positive bacteria, the activity of SC78 and SC5005 against Gram-negative bacteria was also investigated. The MICs of SC78 and SC5005 against *Escherichia coli* (ATCC 25922), *Salmonella Typhimurium* (ATCC 14028), and *Acinetobacter baumannii* (BCRC 80276) were assayed. As the results shown in table 4, SC78 and SC5005 didn't exhibit inhibitory effect on Gram-negative bacteria tested, as demonstrated with MICs over 64 mg/L. Thus, the antibacterial activity of SC78 and SC5005 is specific to Gram-positive bacteria and Mycobacteria.

SC78 and SC5005 are Bactericidal Against *S. aureus*

Figure 2:
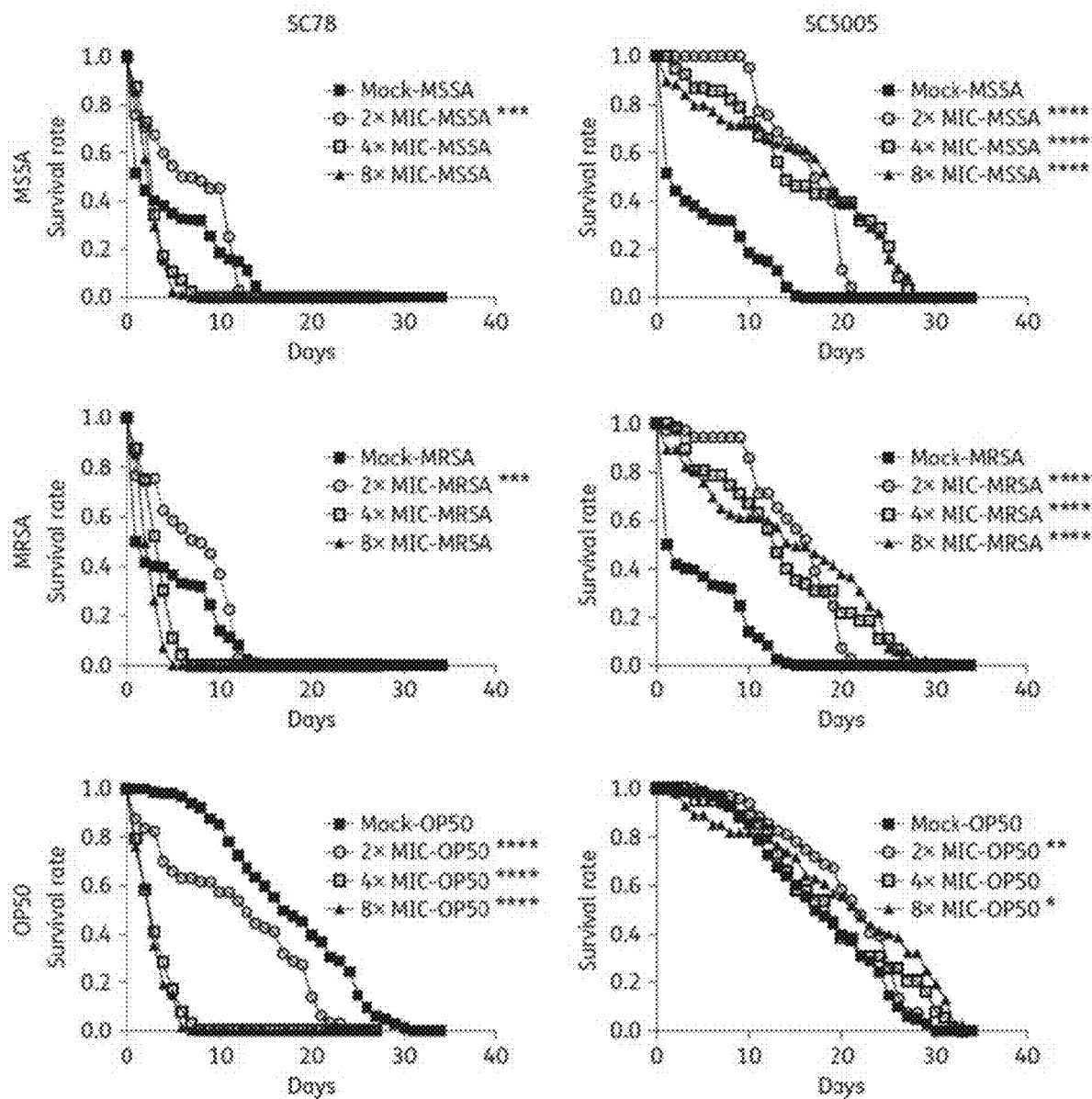
FIG. 2. SC5005 protects *C. elegans* from *S. aureus* infection. Effect of SC78 and SC5005 on the survival of MSSA- or MRSA-infected *C. elegans* was assessed. The glp-4(bn2) *C. elegans* were fed on *E. coli* (OP50), MSSA (ATCC 29213) or MRSA (ATCC 33592) followed by exposing to SC78 or SC5005 at concentrations of 2-, 4-, 8-folds of respective MIC in S-medium. The survival of worms was monitored daily till the end of the study. The survival of animals fed with *E. coli* (OP50) and receiving DMSO only was served as a control to show the normal life-span of *C. elegans*.

An antibacterial agent is considered as bactericidal if it is capable of killing over 99.9% of bacterial inoculum within a 24 hours period of exposure. Otherwise, it is considered bacteriostatic. To investigate the property of SC78 and SC5005, their time-kill kinetics were assessed in *S. aureus* NCTC 8325 over a 24-h treatment period. Overnight-grown bacteria were inoculated in CAMHB at a concentration of $5 \times 10^5$ CFU/ml followed by exposure to individual compounds at concentrations of 2- to 8-folds of respective MIC. As shown in FIG. 2, SC5005 can cause reductions in CFU of 99.91% and 99.95% at concentrations of 4- and 8-folds of MIC, respectively. In contrast, SC78 only caused an over 99.9% reduction of bacteria population at concentration of 8×MIC. According to the finding above, compounds SC78 and SC5005 can be classified as bactericidal.

SC5005 Kills *S. aureus* in the Biofilm

A biofilm is composed of attached microorganisms enclosed in an extracellular polymeric substance matrix. Bacteria embedded in the biofilm are protected from antibiotic-mediated killing and the immune response. Reports have shown that biofilm formation is an important factor contributing to *S. aureus* infections of the skin, lung and indwelling medical devices such as catheters. Thus, the effect of SC5005 on MRSA in a biofilm was assayed. The results indicated that SC5005 possesses superior biofilm-eradicating activity compared with vancomycin, linezolid and daptomycin, as demonstrated by the minimal biofilm eradication concentration (MBEC) of each agent (16 mg/L versus >1024, 1024 and 1024 mg/L, respectively) (Table 5).

TABLE 5

The antibacterial activities of test agents against MRSA in the biofilm.

| | MRSA (ATCC 43300) | |
|---|---|---|
| Test agents | MBEC (mg/L) | MIC (mg/L) |
| SC5005 | 16 | 0.5 |
| Linezolid | >1024 | 1 |
| Daptomycin | 1024 | 0.5 |
| Vancomycin | 1024 | 1 |

SC5005 Protects *C. elegans* from *S. aureus* Infection

Figure 3:
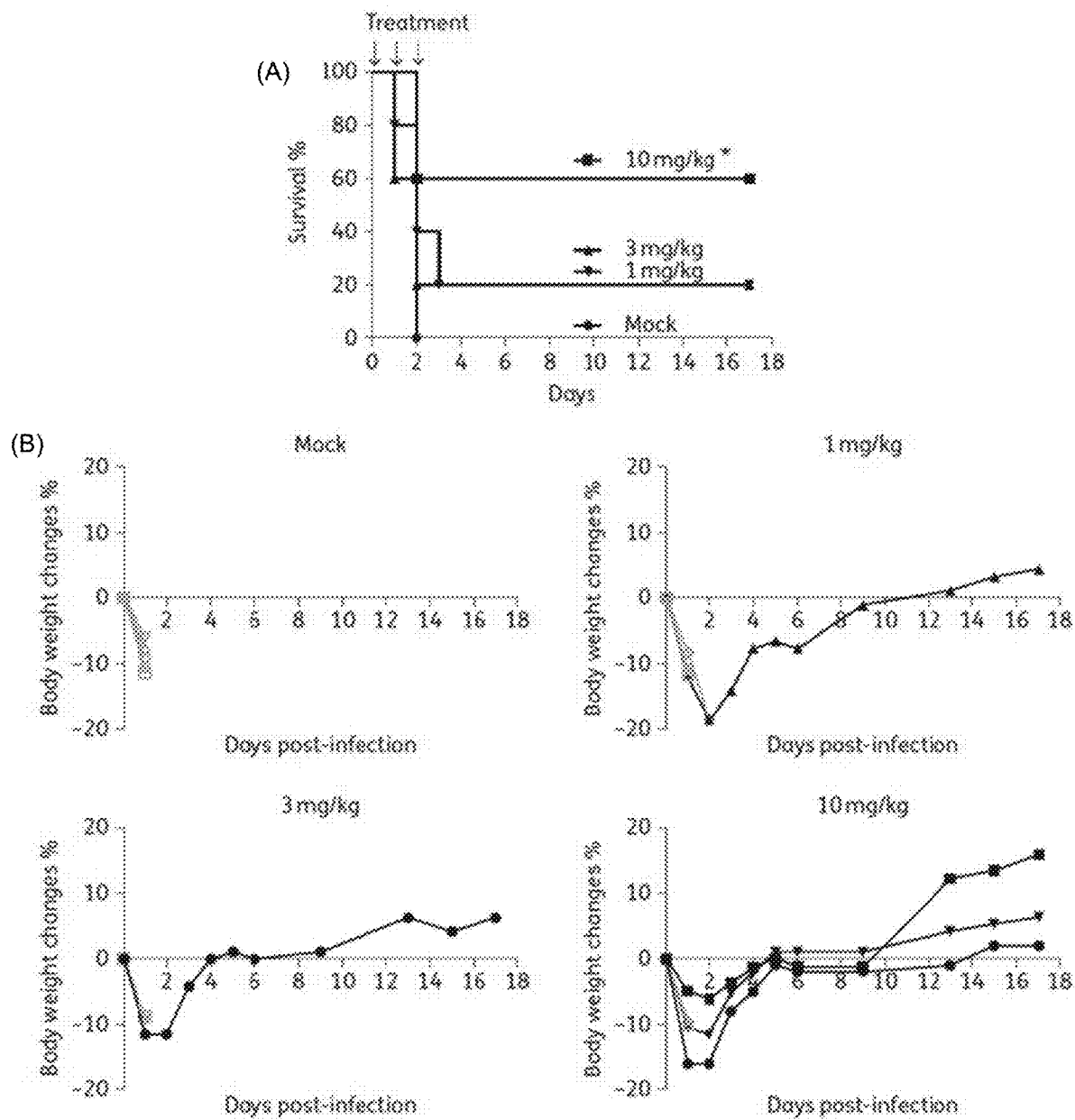
FIG. 3. Intraperitoneal administration of SC5005 improves the survival of MRSA-infected mice. (A) Effect of intraperitoneal administration of SC5005 on the survival of MRSA-infected mice. Female $C_{57}BL/6$ mice were inoculated intraperitoneally with $5×10^4$ CFU of MRSA (ATCC 33592). Infected mice received intraperitoneal injection of 1 mg/kg (filled inverted triangles), 3 mg/kg (filled triangles) and 10 mg/kg (filled squares) SC5005 or vehicle (mock) (filled circles) once per day for three consecutive days. Survival rates, as represented by Kaplan-Meier curves, are shown for the mock and SC5005 treatment groups. *P<0.05, for the difference between treated groups and the control group. (B) Body weight changes in individual vehicle or SC5005-treated MRSA-infected mice. Each line represents an individual mouse. The black lines indicate mice that survived until the end of the study and the grey lines indicate mice that were euthanized during the study.

*Caenorhabditis elegans* has been broadly used as a model host for the studies of human infectious diseases, including infections caused by *S. aureus*. To investigate whether SC78 and SC5005 can suppress the infection of *S. aureus* in *C. elegans*, worms were infected with MSSA ATCC 29213 or MRSA ATCC 33592 followed by exposing to individual drugs at concentrations of 2- to 8-folds of respective MIC in S-medium. Control groups were treated with DMSO at concentration equal to that of drug treated groups (final concentration, 0.1%). As results shown in FIG. 3, no significant difference was observed in the survival of MSSA- or MRSA-infected worms receiving SC78 treatment. In contrast, SC5005 at concentration of 2×MIC already showed strong protective effect, as demonstrated by the significant increase in the mean survival of drug-treated worms comparing to that of *S. aureus* infected worms with control treatment (FIG. 3(B)).

Meanwhile, the toxic effects of these agents on *C. elegans* were also assessed. *E. coli* (OP50)-fed worms were exposed to escalating doses of SC78 and SC5005 in S-medium followed by monitoring of their survival daily. As results shown in FIG. 3, the survival of worms fed with OP50 was significantly decreased with exposure to SC78, suggesting that SC78 is toxic to *C. elegans* at concentrations tested. In contrast, exposure to SC5005 didn't affect the survival as well as the life-span of worms, comparing to that of control (FIG. 3(B)). Thus, these results indicated that SC5005 doesn't possess acute toxicity against *C. elegans*, and its antibacterial activity is capable of suppressing *S. aureus* infection in host animals.

Intraperitoneal Administration of SC5005 Improves the Survival of MRSA-Infected C57BL/6 Mice To further evaluate the therapeutic potential of SC5005 against MRSA infection, inbred C57BL/6 mice were intraperitoneally injected with a lethal dose ($5 \times 10^4$ CFU) of MRSA (ATCC 33592), followed by intraperitoneal administration of vehicle control or SC5005 (1 mg/kg, 3 mg/kg or 10 mg/kg) at 1 h, 24 h and 48 h post-infection (N=5 for each group). Mice infected with MRSA rapidly developed signs of severe infection that included weight loss of over 20%, significant decrease in body temperature, and lethargy (FIG. 4(B)). Survival time for the mice received vehicle was no more than 2 days (FIG. 4(A)). In contrast, three of the mice receiving SC5005 at 10 mg/kg survived till the end of the study, exhibiting decreases of body weight at 1 day post-infection and returned to pre-infection levels after 2-5 days. In addition, only one in each group of mice receiving 1 mg/kg or 3 mg/kg of SC5005 survived after the treatment, suggesting that the effect of SC5005 is dose-dependent and the $ED_{50}$ (defined as effective dose for 50% of the group) of SC5005 is near 10 mg/kg. Together, these findings provided a proof-of-concept that SC5005 exhibited anti-*Staphylococcus* activity in vivo.

Structure Activity Relationship of Malonamide Derivatives

Malonamide derivatives were screened against a panel S. aureus strains, including MSSA 8325, MSSA 29213, MRSA 33592, and MRSA SCCmecVT, for growth-inhibitory activities. The MIC of each agent was determined following the guidelines of the Clinical and Laboratory Standards Institute (CLSI). For the broth microdilution method, overnight grown bacteria on Luria Bertani (LB; Athena Enzyme Systems, Baltimore, Md.) agar plates were suspended in phosphate-buffered saline (PBS) to an O.D. of 1.0 at 600 nm, which was equivalent to $5 \times 10^8$ CFU/ml, and then diluted in cation-adjusted Müller Hinton broth (CAMHB; Difco Laboratories, Detroit, Mich.) to a final concentration of $5 \times 10^5$ CFU/ml. The bacterial suspensions were exposed to the test agents and chloramphenicol at escalating doses, ranging from 0.125 to 64 mg/L, in triplicate in 96-well plates, and the plates were incubated at 37° C. for 24 h. The MIC of each agent was defined as the lowest concentration at which no growth of bacteria was observed.

For agar dilution method, the bacterial suspensions in CAMHB were inoculated at $10^4$ CFU/spot on LB agar plates containing escalating doses of the test agents ranging from 0.125 to 8 mg/L, in triplicate, and the plates were incubated at 37° C. for 24 h. The MIC of each agent was defined as the lowest concentration at which no colony of bacteria was observed (Table 6).

TABLE 6

The growth-inhibitory activities of test agents against S. aureus strains.

| Compound No | MIC (µg/ml) | | | |
| --- | --- | --- | --- | --- |
| | MSSA NCTC 8325 | MSSA ATCC 29213 | MRSA ATCC 33592 | SCCmec $V_T$ |
| SC5020 | >8 | — | — | — |
| SC5021 | 8 | — | — | — |
| SC5022 | >8 | — | — | — |
| SC5023 | 2 | — | 1 | — |
| SC5024 | 1 | — | 1 | — |
| SC5025 | 0.25 | — | 0.25 | — |
| SC5026 | >8 | — | — | — |
| SC5027 | >8 | — | — | — |
| SC5028 | >64 | — | — | — |
| SC5029 | 8 | — | — | — |
| SC5030 | >16 | — | — | — |
| SC5031 | >64 | — | — | — |
| SC5032 | 32 | — | — | — |
| SC5033 | 32 | — | — | — |
| SC5034 | 1 | — | — | — |
| SC5035 | 0.25 | — | 0.25 | — |
| SC5036 | 0.25 | — | 0.5 | — |
| SC5037 | 8 | — | >32 | — |
| SC5038 | >32 | — | >32 | — |
| SC5039 | >32 | — | >32 | — |
| SC5040 | >32 | — | >32 | — |
| SC5041 | 0.5 | — | 0.5 | — |
| SC5005 | 0.5 | 0.5 | 0.5 | 0.5 |
| SC5046 | >64 | — | >64 | — |
| SC5047 | >64 | — | >64 | — |
| SC5048 | >64 | — | >64 | — |
| SC5049 | >64 | — | >64 | — |
| SC50SC50 | >64 | — | >64 | — |
| SC5051 | >64 | — | >64 | — |
| SC5052 | >64 | — | >64 | — |
| SC5053 | >64 | — | >64 | — |

Drug Resistance of S. aureus NCTC 8325 Against SC78 and SC5005

Figure 4:
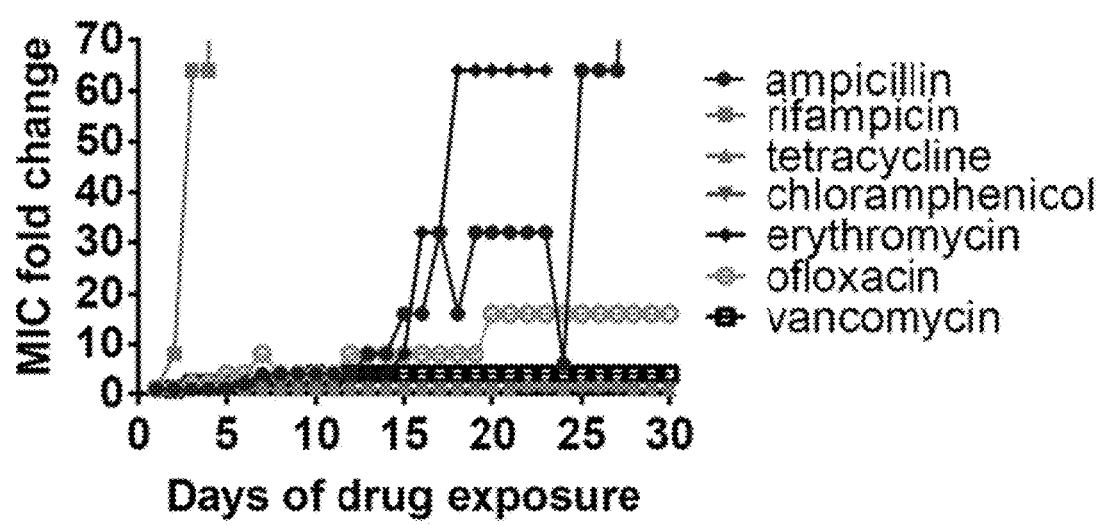
FIG. 4. Resistance of *S. aureus* NCTC 8325 to SC78, SC5005 and seven common antibiotics. *S. aureus* NCTC 8325 were cultured in CAMHB with test agents at escalating concentrations in wells of a 96 well-plate. After 24 hours incubation at 37° C., bacteria from the sub-MIC well were 1:1000 diluted in fresh CAMHB with test agents at escalating concentrations for another 24 hours. To select for strains resistant to (A) seven antibiotics, (B) SC78 or SC5005, the experiment was repeated for 30 days and 200 days, respectively. Data was presented as fold change in the MIC compared to that at initial.
Figure 4:
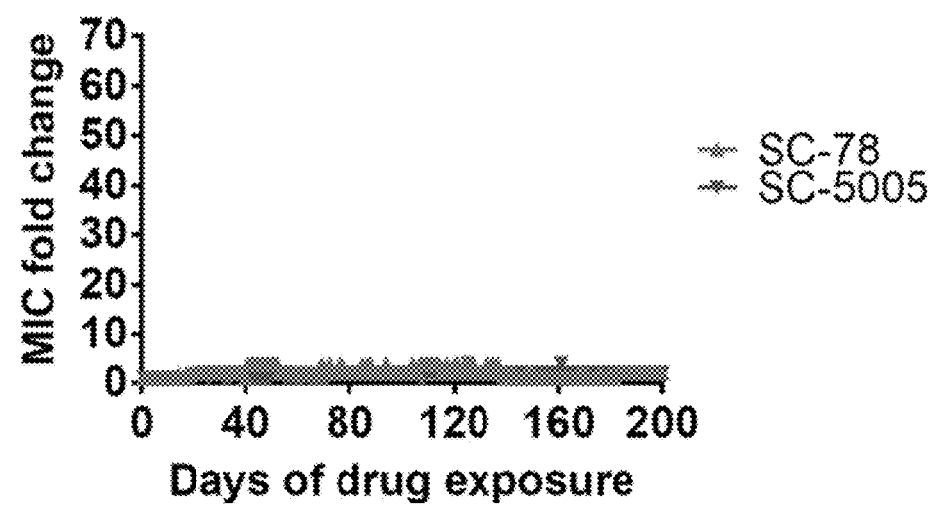

To investigate the resistance of S. aureus against SC78 and SC5005, the bacteria were cultured at a sub-inhibitory concentration of antibiotics for 30 consecutive days. As shown in FIG. 4(A), S. aureus developed resistance to rifampicin, erythromycin, and ampicillin over 64-fold MIC change within 6 days, 17 days, and 27 days, respectively. There are also 8- and 4-fold MIC change in ofloxacin and vancomycin. In contrast, no resistance to chloramphenicol and tetracycline were observed in this period. It is noteworthy that no resistance was observed even after a 200-day consecutive exposure to sub-lethal concentrations of SC78 and SC5005 (FIG. 4). According to the results above, S. aureus is unable to develop resistance to SC78 and SC5005.

Figure 5:
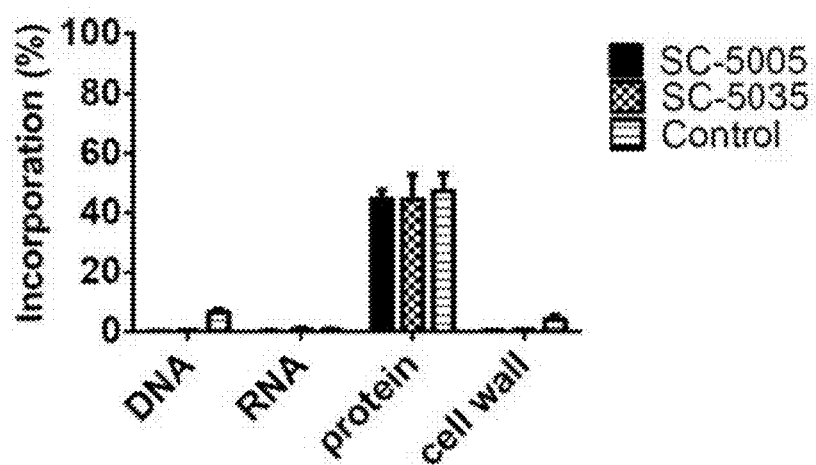
FIG. 5. Effect of SC5005 and SC5035 on the biosynthesis of macromolecules in *S. aureus*. The biosynthesis of macromolecules in *S. aureus* was assayed by measuring the incorporation of 3H-thymidine (DNA), 3H-uridine (RNA), 3H-leucine (protein), and 3H—N-acetylglucosamine (cell wall) into bacteria cells treated with 4×MIC of SC5005 (2 mg/L), SC5035 (1 mg/L) for 1 h. Meanwhile, ofloxacin (1 mg/L), rifampicin (1 mg/L), erythromycin (2 mg/L), and vancomycin (2 mg/L) were used as control inhibitors for the biosynthesis of DNA, RNA, protein and cell wall, respectively. Data are means of three independent experiments. Error bars represent the SD.

SC5005 and SC5035 Inhibit Major the Biosynthesis of Major Macromolecules in S. aureus To investigate the mode of action of SC5005, a new derivative, SC5035, with better selectivity of antibacterial activity over cytotoxicity was included in the assays. First, the impacts of these two compounds on the biosynthesis of important macromolecules, including DNA, RNA, protein and cell wall, in S. aureus NCTC 8325 were assessed. Bacteria cells were incubated with [$^3$H]thymidine to assess DNA synthesis, [$^3$H] uridine to assess RNA synthesis, [$^3$H] leucine to assess protein synthesis, and [$^3$H] N-Acetyl-D-glucosamine to assess cell wall synthesis. The ofloxacin, rifampicin, erythromycin and vancomycin were used as control inhibitor for DNA, RNA, protein, and cell wall biosynthesis, respectively. Inhibition of biosynthesis pathway was determined by a reduction in the radial isotope signal of bacteria. As shown in FIG. 5, bacteria treated with SC5005 and SC5035 showed a lower signal in all four macromolecule biosynthesis pathway, suggesting that the target of SC5005 and SC5035 is upstream of these pathways.

SC5005 and SC5035 Cause ATP Leakage in S. aureus

Figure 6:
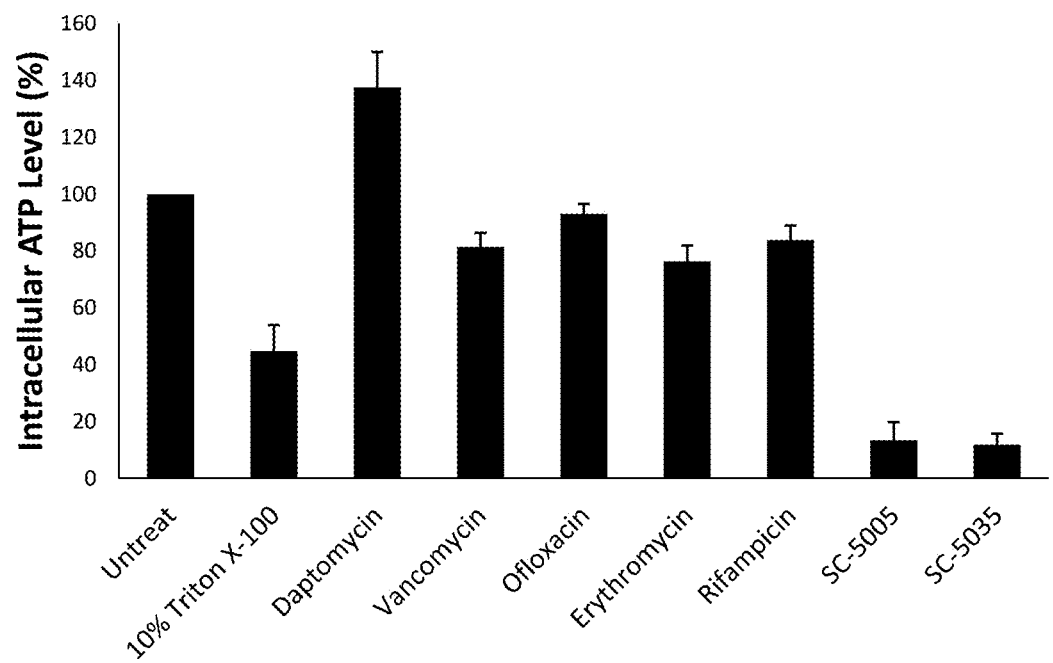
FIG. 6. Intracellular ATP leakage of *S. aureus* treated with SC5005, SC5035 and antibiotics. *S. aureus* NCTC 8325 were treated with SC5005, SC5035 and antibiotics at 4×MIC against *S. aureus* for 15 min followed by measuring the intracellular ATP level with ATPlite one-step kit. Data was presented as percentage of intracellular ATP level to that of untreated bacteria cells (considered as 100%). Bars represent the mean, and error bars represent the SD (n=3). ***: p-value <0.001

Reports indicated that membrane-active antibacterial agent will suppress the biosynthesis of all major macromolecules in bacteria. To investigate whether SC5005 and SC5035 also act on bacterial cell membrane, intracellular ATP levels of S. aureus treated with SC5005, SC5035 and antibiotics for 15 min was determined by using ATPlite one-step assay kit. As result shown in FIG. 6, intracellular ATP levels of bacteria cells treated with SC5005 and SC5035 significantly dropped, suggesting these two compounds caused damage to bacterial cell membrane, and leading to leakage of intracellular components.

SC5005 and SC5035 Disrupt Membrane Integrity of S. aureus

Figure 7:
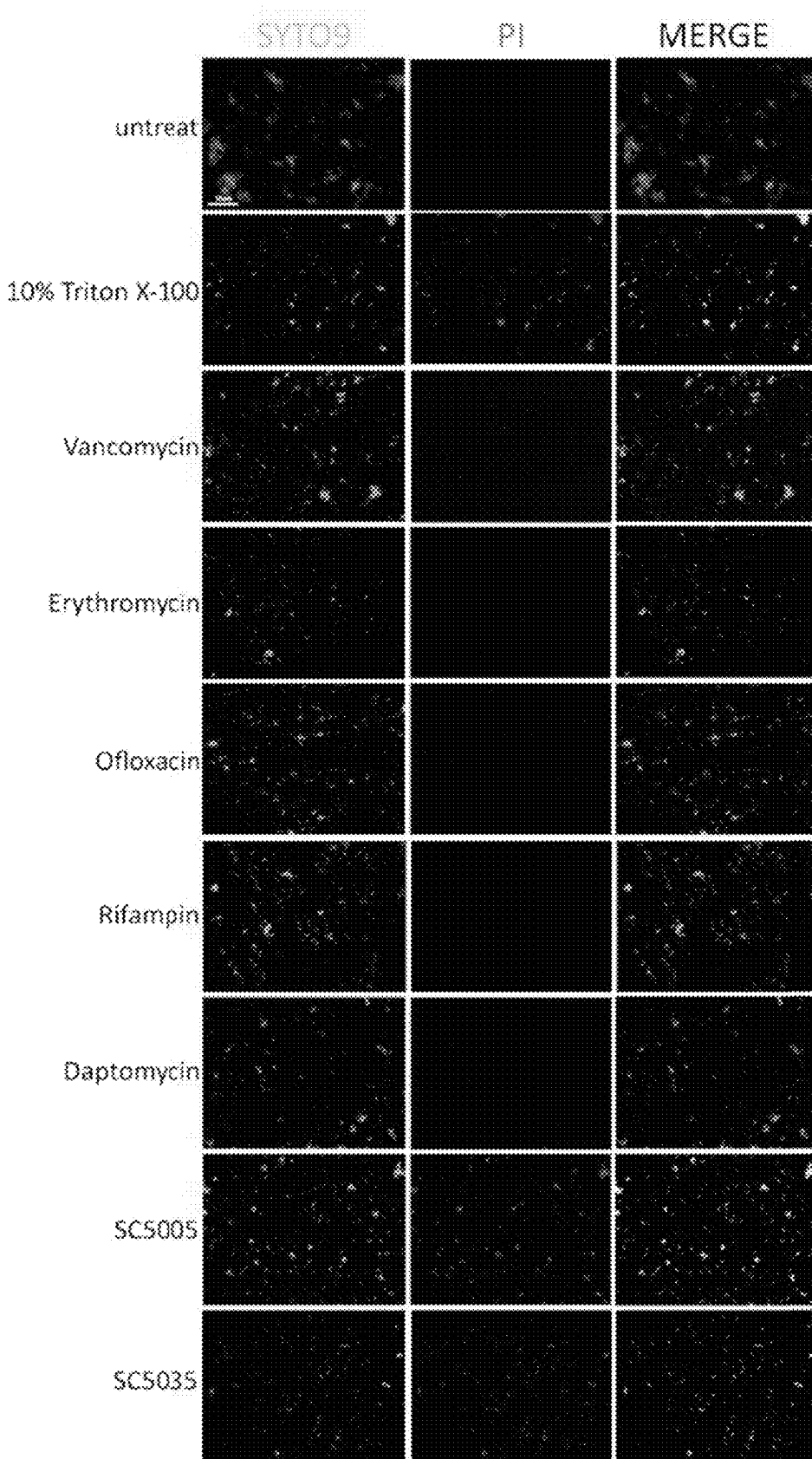
FIG. 7. Membrane integrity of *S. aureus* after SC5005, SC5035 and five common antibiotics treatment. *S. aureus* NCTC 8325 were treated with 10% Triton X-100, or 4×MIC of test agents against *S. aureus* for 15 minutes followed by chromosome staining with LIVE/DEAD Baclight kit. SYTO 9, a green fluorescence dye, stains chromosome of all bacteria cells, regardless of the membrane integrity. In contrast, propidium iodide (PI), a red fluorescence dye, only stains cell with damaged membrane. Thus, bacteria cell with intact membrane can only be stained by SYTO 9, and cell with perforated membrane will be stained by both fluorescence dyes, showing a yellow color in merged images.

To further validate the action mechanism of SC5005 and SC5035, two fluorescence dyes were used for evaluation of membrane integrity of drug treated S. aureus. The propidium iodide dye only stains cells with perforated membrane, while the SYTO 9 stains all cells in spite of membrane integrity. Result showed that only S. aureus treated with 10% Triton X-100, SC5005 and SC5035 can be stained by propidium iodide, indicating these two compounds can disrupt membrane integrity of S. aureus (FIG. 7).

SC5005 Causes Pore-Formation in Membrane of S. aureus

Figure 8:
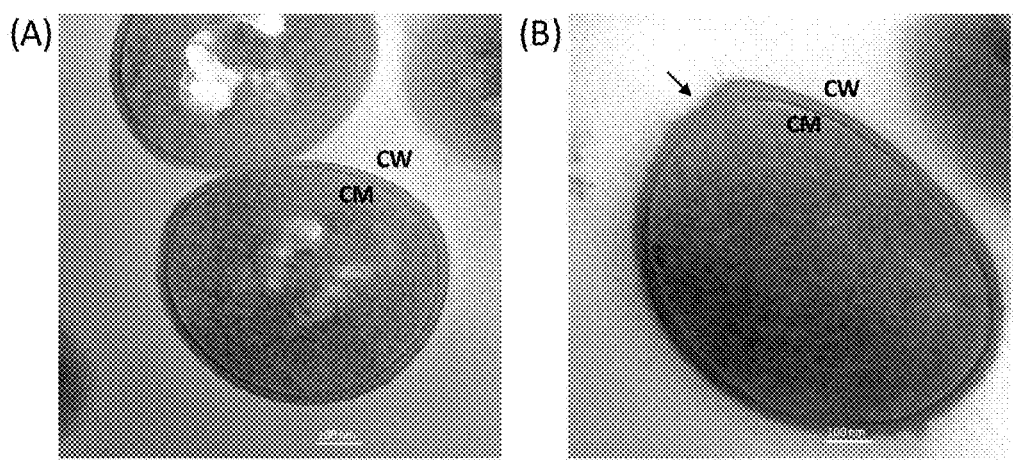
FIG. 8. Transmission electron microscopy image of *S. aureus* after SC5005 treatment. *S. aureus* NCTC 8325 was treated with (A) mock or (B) SC5005 for 15 min followed by glutaraldehyde (2.5%) fixation and osimium tetraoxide (1%) staining. The membrane integrity was then observed with transmission electron microscopy at 100,000× magnification. The outer black ring marked with CW represents cell wall, and the inner black ring marked with CM represents cell membrane. The arrow points the pore formed in *S. aureus* cell membrane.

To investigate how SC5005 changes membrane permeability of S. aureus, bacteria cells were treated with SC5005 for 15 min followed by glutaraldehyde (2.5%) fixation and osimium tetraoxide (1%) staining. The membrane of bacteria was then observed by Transmission electron microscopy (TEM) at 100,000 magnifications (FIG. 8). The outer clear black circle is cell wall of S. aureus, and the inner clear black circle is cell membrane of S. aureus. These two circles of control treated S. aureus remain intact, and the cell membrane is undamaged. In contrast, a pore was observed in the membrane of most bacteria cells treated with SC5005. This data indicated that SC5005 can cause pore forming in the membrane of S. aureus.

SC5005 and SC5035 Doesn't Cause Hemolysis of Human Red Blood Cell

Figure 9:
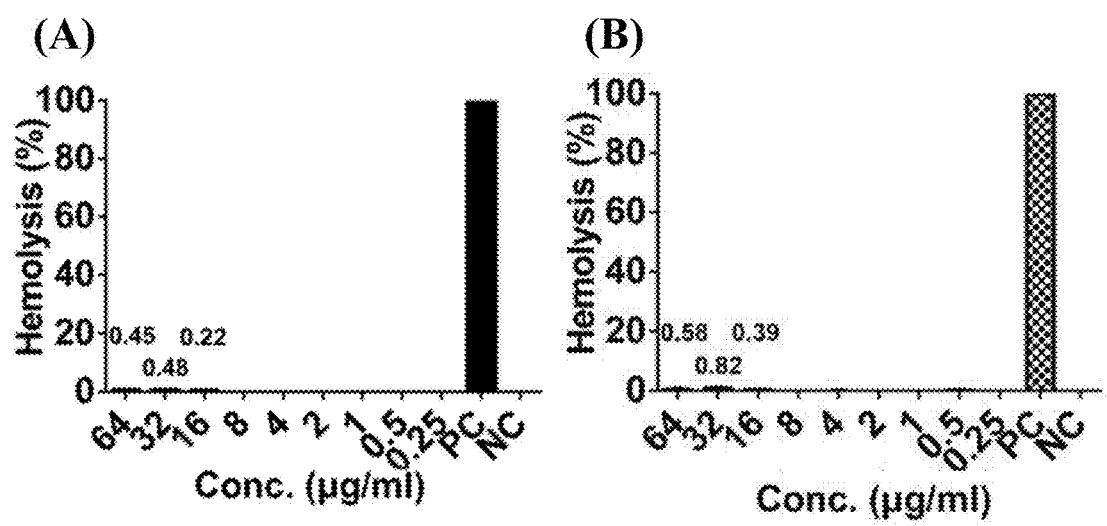
FIG. 9. Hemolytic activities of SC5005 and SC5035 on human red blood cell. Human red blood cells were incubated with SC5005 (A) and SC5035 (B) for 1 h followed by measuring the absorption of RBC released hemoglobin at 540 nm with microplate reader. Cell treated with 1% triton X-100 serves as positive control (P.C.; 100% hemolysis), and those treated with normal saline serves as negative control (N.C.) Bars represent the mean, and error bars represent the SD (n=3).
Figure 10:
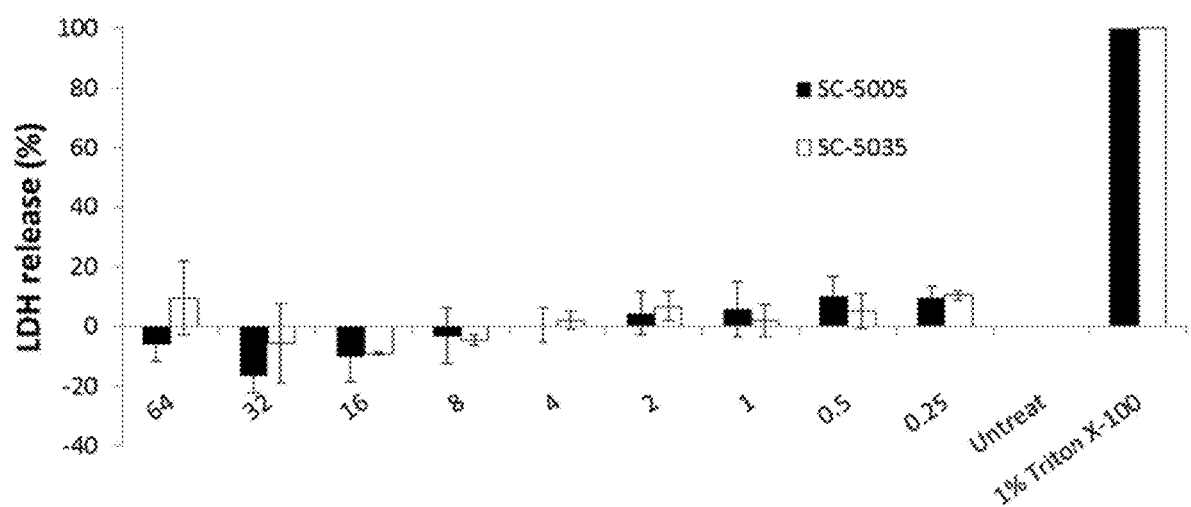
FIG. 10. Membrane integrity of human cells treated with SC5005 and SC5035. Human HT-29 cells were treated with SC5005 and SC5035 for 1 hour followed by the evaluation of membrane integrity with LDH release assay. LDH released from HT-29 cells into culture medium was assessed by using CytoTox 96 NonRadioactive Cytotoxicity Assay. Cell treated with 1% triton X-100 serves as positive control (100% release). Bars represent the mean, and error bars represent the SD (n=3).

As data shown above, SC5005 and SC5035 can kill bacteria via forming pore in bacterial membrane. To see whether the pore-forming activity of these two compounds is specific for bacterial membrane, the hemolytic activities of these two agents on human red blood cells were accessed. As result shown in FIG. 9, no significant hemolysis was observed of RBC treated with SC5005 or SC5035 at the concentration up to 128-fold of their MIC against S. aureus. SC5005 and S5035 Doesn't Disrupt Membrane Integrity of Human Cells To further validate the activity of SC5005 and SC5035 on the membrane of human cells, the integrity of cellular membrane of cells treated with these two compounds was assessed by using LDH release assay. Human HT-29 cells were treated with SC5005 and SC5035 for 1 hour, and then the LDH released from cell into culture medium was assayed. The results indicated that no significant increase in the LDH level of cells treated with SC5005 and SC5035 at the concentration up to 128-fold of their MIC against S. aureus (FIG. 10). Together, results of RBC hemolysis assay and LDH release assay indicated that the pore-forming activity of SC5005 and SC5035 is highly specific to bacteria membrane.

What is claimed is:

1. A substituted malonamide having a chemical structure (I):

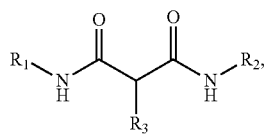

wherein $R_1$ is

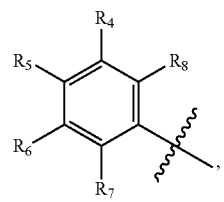

$C_{2-6}$ alkyl, $C_{2-6}$ alkenyl, or $C_{3-7}$ cycloalkyl;
$R_2$ is

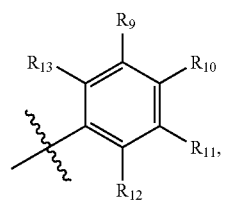

$C_{2-6}$ alkyl, $C_{2-6}$ alkenyl, or $C_{3-7}$ cycloalkyl;
$R_3$ is selected from $C_3$ cycloalkyl, $C_{2-6}$ alkenyl, or $C_{2-5}$ halogenoalkyl;
$R_4$, $R_5$, $R_6$, $R_7$, $R_8$, $R_9$, $R_{10}$, $R_{11}$, $R_{12}$, and $R_{13}$ are independently selected from hydrogen, $C_{1-5}$ alkyl, $C_{2-6}$ alkenyl, ethynyl, halogen, trihalogenomethyl, nitro, hydroxyl, trihalogenomethoxy, or pentafluorosulfanyl;
if $R_3$ is allyl, $R_1$ and $R_2$ are not 2,4-dichlorophenyl and 2,5-dichlorophenyl; if $R_3$ is $C_{3-5}$-halogenoalkyl, $R_1$ and $R_2$ are not independently selected from phenyl, $C_{1-5}$-alkyl phenyl or halogen phenyl; if $R_4$, $R_5$, $R_6$, $R_7$, $R_8$, $R_9$, $R_{10}$, $R_{11}$, $R_{12}$, and $R_{13}$ are hydrogen, $R_3$ is not allyl or dimethylallyl.

2. The substituted malonamide of claim 1, wherein $R_1$, and $R_2$ are independently selected from

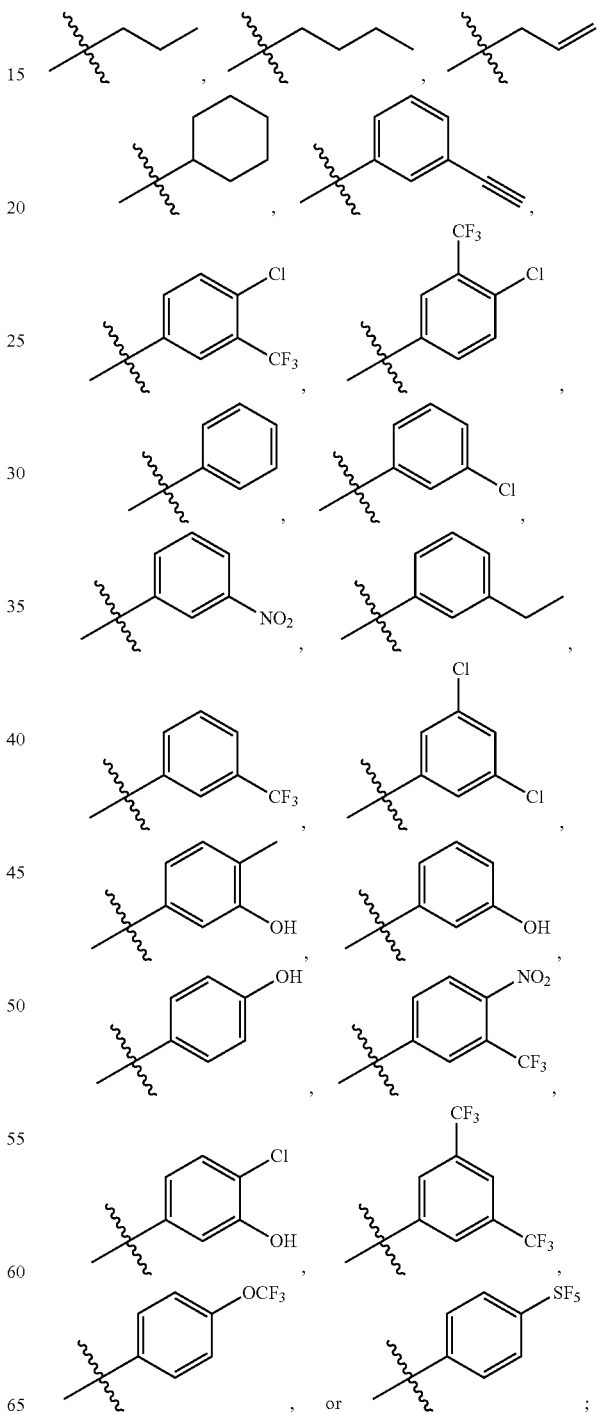

R₃ is selected from

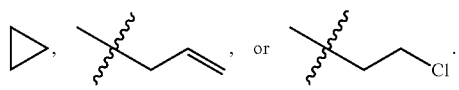

3. A pharmaceutical composition comprising:
an effective amount of a compound having a chemical structure (I):

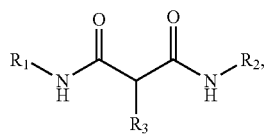

wherein R₁

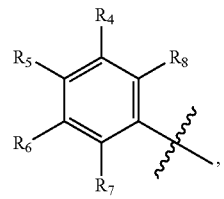

$C_{2-6}$ alkyl, $C_{2-6}$ alkenyl, or $C_{3-7}$ cycloalkyl;
R₂ is

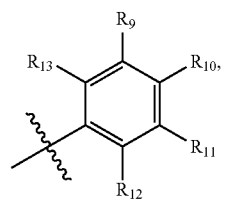

$C_{2-6}$ alkyl, $C_{2-6}$ alkenyl, or $C_{3-7}$ cycloalkyl;
R₃ is selected from $C_3$ cycloalkyl, $C_{2-6}$ alkenyl, or $C_{2-5}$ halogenoalkyl;
R₄, R₅, R₆, R₇, R₈, R₉, R₁₀, R₁₁, R₁₂, and R₁₃ are independently selected from hydrogen, $C_{1-5}$ alkyl, $C_{2-6}$ alkenyl, ethynyl, halogen, trihalogenomethyl, nitro, hydroxyl, trihalogenomethoxy, or pentafluorosulfanyl;
and a pharmaceutically acceptable carrier; if R₃ is allyl, R₁ and R₂ are not 2,4-dichlorophenyl and 2,5-dichlorophenyl; if R₃ is $C_{3-5}$-halogenoalkyl, R₁ and R₂ are not independently selected from phenyl, halogen phenyl, or $C_{1-5}$-alkyl phenyl; if R₄, R₅, R₆, R₇, R₈, R₉, R₁₀, R₁₁, R₁₂, and R₁₃ are hydrogen, R₃ is not allyl or dimethylallyl.

4. The pharmaceutical composition of claim 3, wherein R₁, and R₂ are independently selected from

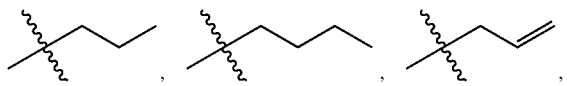

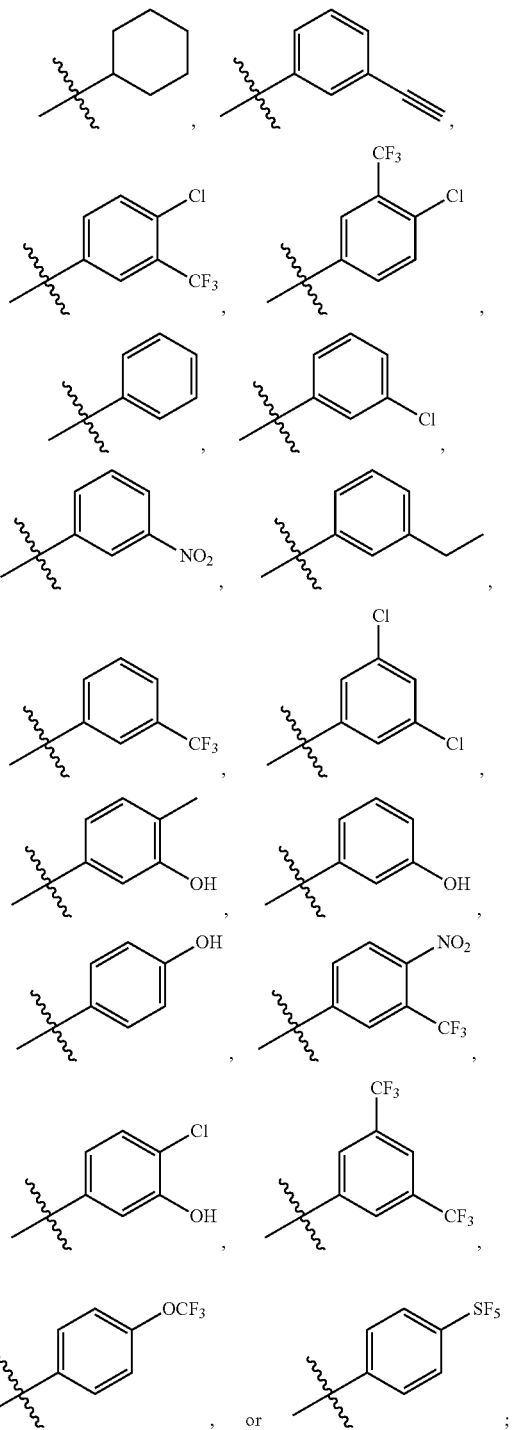

R₃ is selected from

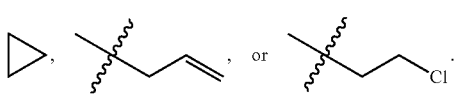

5. The pharmaceutical composition of claim 3, wherein the compound having a chemical structure (I) is:

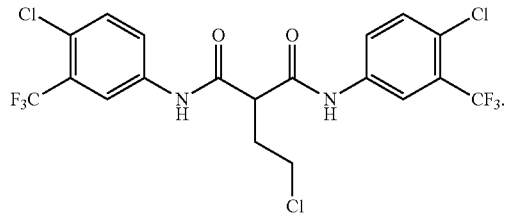

(V)

6. A method of inhibiting bacterial cell growth, comprising: contacting bacterial cell with an effective amount of a compound having a chemical structure (I):

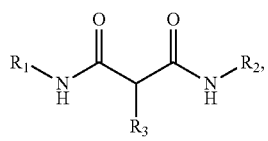

(I)

wherein R₁ is

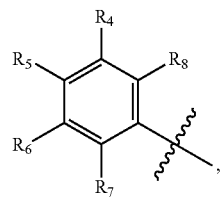

$C_{2-6}$ alkyl, $C_{2-6}$ alkenyl, or $C_{3-7}$ cycloalkyl;
R₂ is

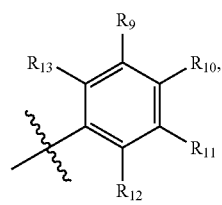

$C_{2-6}$ alkyl, $C_{2-6}$ alkenyl, or $C_{3-7}$ cycloalkyl;
R₃ is selected from C₃ cycloalkyl, $C_{2-6}$ alkenyl, or $C_{2-5}$ halogenoalkyl;
R₄, R₅, R₆, R₇, R₈, R₉, R₁₀, R₁₁, R₁₂, and R₁₃ are independently selected from hydrogen, $C_{1-5}$ alkyl, $C_{2-6}$ alkenyl, ethynyl, halogen, trihalogenomethyl, nitro, hydroxyl, trihalogenomethoxy, or pentafluorosulfanyl,
if R₃ is allyl, R₁ and R₂ are not 2,4-dichlorophenyl; if R₃ is 1-halogenopentane, R₁ and R₂ are not independently selected from phenyl, $C_{1-5}$-alkyl phenyl or halogen phenyl; if R₄, R₅, R₆, R₇, R₈, R₉, R₁₀, R₁₁, R₁₂, and R₁₃ are hydrogen, R₃ is not allyl or dimethylallyl.

7. The method of claim 6, wherein R₁, and R₂ are independently selected from

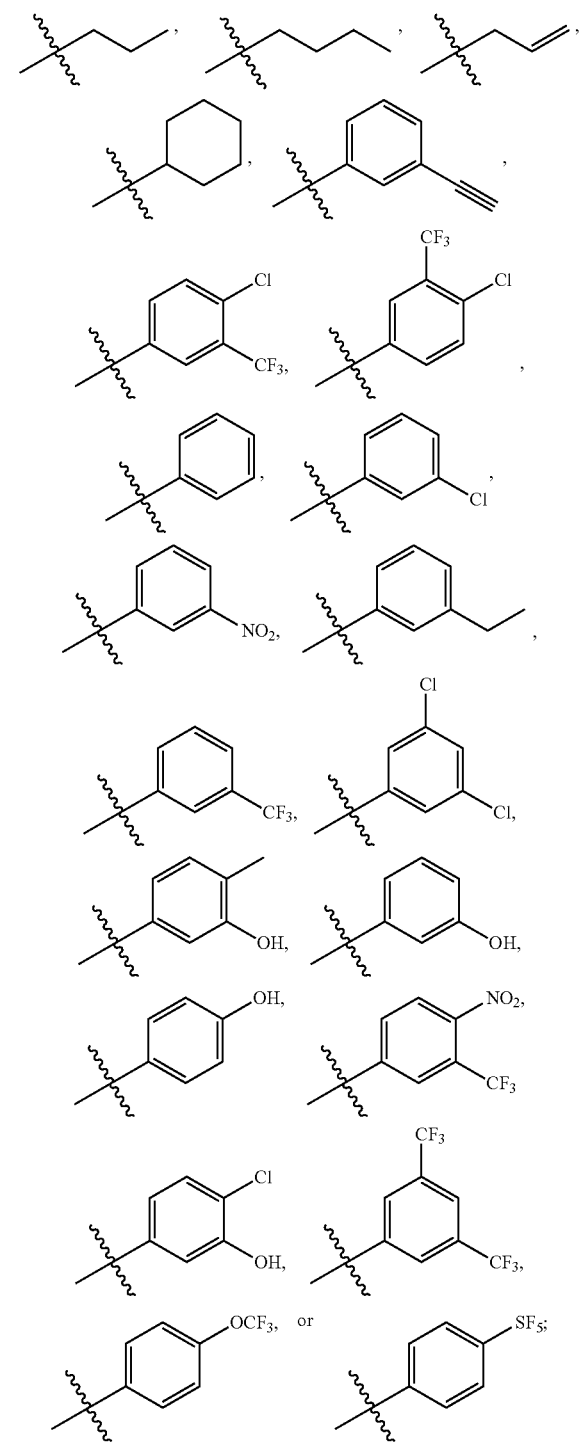

R₃ is selected from

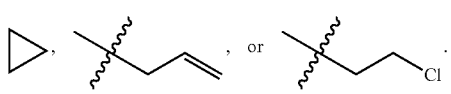

8. The method of claim 6, wherein the compound having a chemical structure (I) is:

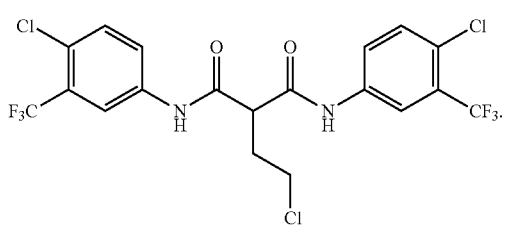
(V)

9. The method of claim 6, wherein the bacterial cells are cells of human pathogenic bacteria.

10. The method of claim 6, wherein the human pathogenic bacteria are selected from the group consisting of *Staphylococcus aureus, Staphylococcus haemolyticus, Staphylococcus hominis, Staphylococcus intermedius, Staphylococcus saprophyticus, Staphylococcus lugdunesis, Erysipelothrix rhusiopathiae, Enterococcus faecalis, Enterococcus faecium, VR-E. faecium, Bacillus cereus, Bacillus subtilis, Corynebacterium diphtheriae, Listeria monocytogenes, Streptococcus pyogenes, Clostridium difficile, Escherichia coli, Salmonella Typhimurium, Acinetobacter baumannii*, and *Mycobacterium tuberculosis*.

11. A method of synthesizing the substituted malonamide of claim 1, comprising:

(a) reacting a compound having chemical structure (II) with a first substituted amine $R_1$—$NH_2$ to obtain a compound having chemical structure (III),

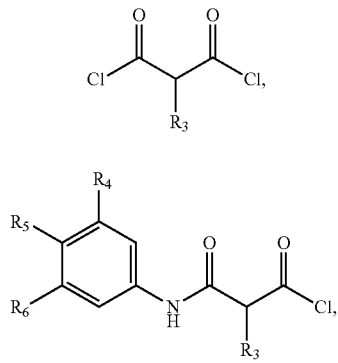
(II)

(III)

(b) the compound having chemical structure (III) further reacts with a second substituted amine $R_2$—$NH_2$ to obtain the substituted malonamide of claim 1, wherein $R_1$ is

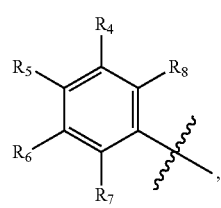

$C_{2-6}$ alkyl, $C_{2-6}$ alkenyl, or $C_{3-7}$ cycloalkyl;

$R_2$ is

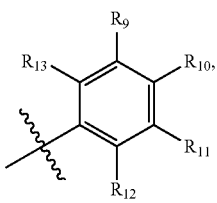

$C_{2-6}$ alkyl, $C_{2-6}$ alkenyl, or $C_{3-7}$ cycloalkyl;

$R_3$ is selected from $C_3$ cycloalkyl, $C_{2-6}$ alkenyl, or $C_{2-5}$ halogenoalkyl;

$R_4$, $R_5$, $R_6$, $R_7$, $R_8$, $R_9$, $R_{10}$, $R_{11}$, $R_{12}$, and $R_{13}$ are independently selected from hydrogen, $C_{1-5}$ alkyl, $C_{2-6}$ alkenyl, ethynyl, halogen, trihalogenomethyl, nitro, hydroxyl, trihalogenomethoxy, or pentafluorosulfanyl;

wherein $R_1$ and $R_2$ are different substituted groups.

12. The method of claim 11, wherein $R_1$, and $R_2$ are independently selected from

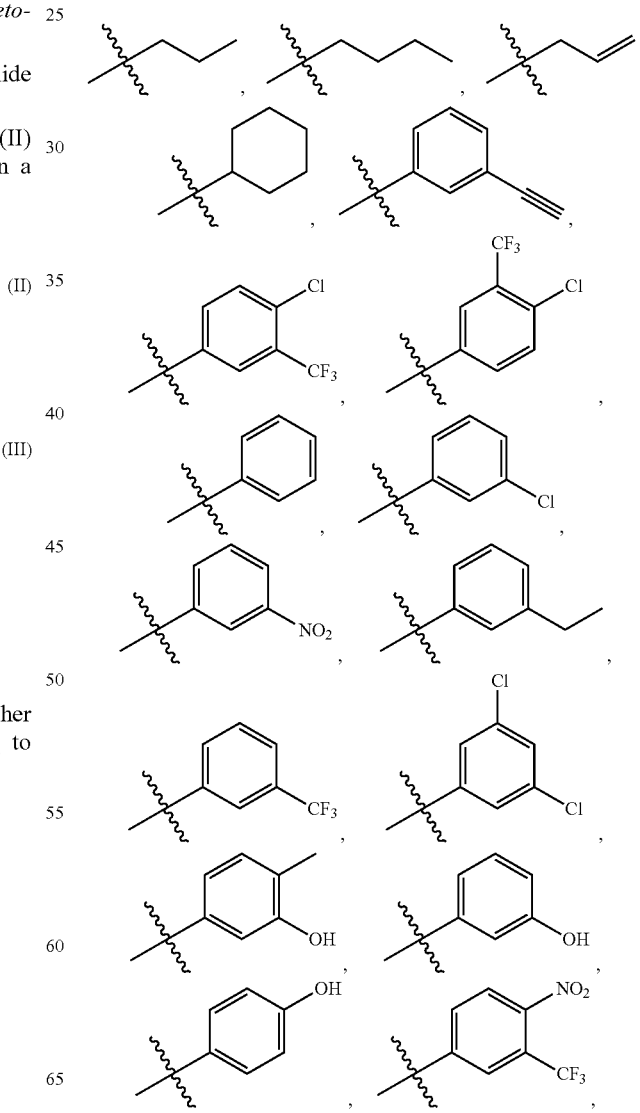

-continued
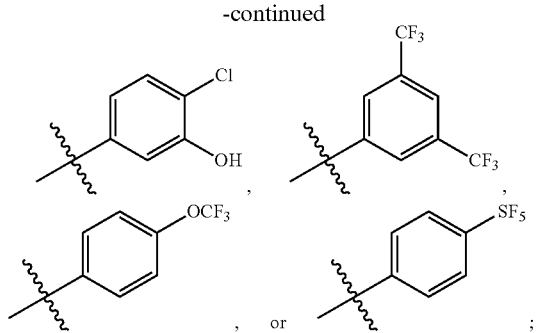
$R_3$ is selected from
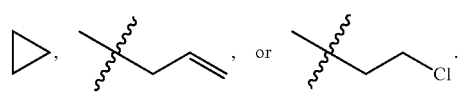
* * * * *